US006703494B2

(12) United States Patent
Kirchhofer et al.

(10) Patent No.: US 6,703,494 B2
(45) Date of Patent: Mar. 9, 2004

(54) ANTI-TISSUE FACTOR ANTIBODIES WITH ENHANCED ANTICOAGULANT POTENCY

(75) Inventors: Daniel K. Kirchhofer, Los Altos, CA (US); David G. Lowe, Hillsborough, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/802,083

(22) Filed: Mar. 8, 2001

(65) Prior Publication Data

US 2003/0119075 A1 Jun. 26, 2003

Related U.S. Application Data

(60) Provisional application No. 60/189,775, filed on Mar. 16, 2000.

(51) Int. Cl.$^7$ .................... C12N 15/13; C12N 15/12; C12N 15/00; C07K 16/24

(52) U.S. Cl. ............ 536/23.5; 536/23.1; 530/387.1; 530/387.3; 530/388.2; 530/388.25; 435/69.6; 435/252.3; 435/320.1; 435/455; 435/326

(58) Field of Search ............... 530/387.1, 387.3, 530/388.2; 435/69.6, 252.3, 455, 326; 536/23.1, 23.5

(56) References Cited

U.S. PATENT DOCUMENTS

| | | | |
|---|---|---|---|
| 5,223,427 | A | 6/1993 | Edgington et al. |
| 5,811,248 | A | 9/1998 | Ditlow et al. |
| 5,986,065 | A | 11/1999 | Wong et al. |
| 6,001,978 | A | 12/1999 | Edgington et al. |
| 6,555,319 | B2 | 4/2003 | Wong et al. |

FOREIGN PATENT DOCUMENTS

| | | |
|---|---|---|
| EP | 266993 | 5/1988 |
| EP | 278776 | 8/1988 |
| EP | 1 069 185 | 1/2001 |
| EP | 1222854 | 7/2002 |
| WO | WO 96/40921 | 12/1996 |
| WO | WO 99/51743 | 10/1999 |

OTHER PUBLICATIONS

Addonizio et al., "Preliminary characterization of the procoagulant material in human ascites" *Surgery* 101(6):753–762 (Jun. 1987).
Albrecht et al., "An ELISA for tissue factor using monoclonal antibodies" *Blood Coagulation and Fibrinolysis* 3:263–270 (1992).
Hancock et al. *Pathology* (28th Annual Meeting of the Royal College of Pathologists of Australasia, Melbourne, Australia) 16(4):479–480 (Oct. 1983).
Hancock W. et al., "Immunohistological Studies with A1–3, A Monoclonal Antibody to Activated Human Monocytes and Macrophages" *The Journal of Immunology* 136(7):2416–2420 (Apr. 1986).
Imamura T. et al., "Role of Macrophage Tissue Factor in the Development of the Delayed Hypersensitivity Reaction in Monkey Skin" *Cellular Immunology* 152:614–622 (1993).
Ito et al., "Characterization of Functionally Important Regions of Tissue Factor by Using Monoclonal Antibodies" *J. Biochemistry* 114:691–696 (1993).
Johnsen, "Platelets Stimulate Thromboplastin Synthesis in Human Endothelial Cells" *Thromb Haemostas* 49(2):67–72 (1983).
Maekawa et al, "Complement–Dependent Immunosuppressive Anti–Tissue Factor Monoclonal Antibody: The Establishment of Monoclonal Antibodies and Their Effect on Mixed Lymphocyte Reaction" *Transplantation Proceedings* 25(4):2713–2715 (Aug. 1993).
Sato et al., "Tissue Factor Induces Migration of Cultured Aortic Smooth Muscle Cells" *Thrombosis and haemostasis* 75(3):389–392 (1996).
Fiore et al., "An Unusual Antibody that Blocks Tissue Factor/Factor VIIa Function by Inhibiting Cleavage Only of Macromolecular Substrates" *Blood* 80(12):3127–3134 (Dec. 15, 1992).
Ruf et al., "An Anti–Tissue Factor Monoclonal Antibody which inhibits TF–VIIa Complex Is a Potent Anticoagulant" *Thrombosis and Haemostasis* 66:529–533 (1991).
Bach et al., "Purification and Characterization of Bovine Tissue Factor" *Journal of Biological Chemistry* 256(16):8324–8331 (1981).
Barker, P. L. et al., "Cyclic RGD Peptide Analogues as Antiplatelet Antithrombotics" *Journal Medicinal Chemistry* 35:2040–2048 (1992).
Bjorklid et al., "Purification and Some Properties of the Protein Component of Tissue Thromboplastin from Human Brain" *Biochemical Journal* 165(1):89–96 (1977).
Bom et al., "Application of Factor VII–Sepharose Affinity Chromatography in the Purification of Human Tissue Factor Apoprotein" *Thrombosis Research* 42:635–643 (1986).
Braunwald et al., "ACC/AHA Guidelines for the Management of Patients With Unstable Angina and Non–ST–Segment Elevation Myocardial Infarction" *Journal of the American College of Cardiology* 36(3):970–1056 (Sep. 2000).
Broze, Jr., et al., "Purification of Human Brain Tissue Factor" *Journal of Biological Chemistry* 260(20):10917–10920 (1985).

(List continued on next page.)

Primary Examiner—Phillip Gambel
(74) Attorney, Agent, or Firm—Elinor K. Shin

(57) ABSTRACT

The invention concerns anti-tissue factor (anti-TF) antibodies with enhanced anticoagulant potency, and methods and means for identifying, producing and using such antibodies. The anti-TF antibodies of the present invention are designed to comprise a region binding to an epitope in the C-terminal macromolecular substrate binding region of TF.

19 Claims, 18 Drawing Sheets

OTHER PUBLICATIONS

Carson et al., "An Inhibitory Monoclonal Antibody Against Human Tissue Factor." *Blood* 70(2):490–493 (1987).

Carson et al., "Monoclonal Antibodies Bovine Tissue Factor, Which Block Interaction with Factor VIIa" *Blood* 66(1):152–156 (1985).

De Guzman et al., "Inhibition of tissue factor or intrinsic XASE are effective antithrombotic strategies in a new model of venous thrombosis" *Thrombosis and Haemostasis Abstracts from XVIth Congress of the International Society on Thrombosis and Haemostasis, Florence, Italy, Jun. 6–12, 1997*, PS–1194:1–844.

Diffang et al, "Effect of Trasylol on Fibrin Deposition and Elimination in the Lungs of Rats with Intravascular Coagulation Induced by Thrombin or Thromboplastin" *Thrombosis Research* 5:263–276 (1974).

Dittmar et al., "Influence of mutations in tissue factor on the fine specificity of macromolecular substrate activation" *Biochemical Journal* 321(3):787–793 (1997).

Guha et al., "Affinity Purification of Human Tissue Factor: Interaction of Factor VII and Tissue Factor in Detergent Micelles." *Proc. Natl. Acad. Sci. USA* 83:299–302 (1986).

Kirchhofer et al., "The Tissue Factor Region that Interacts with Factor Xa in the Activation of Factor VII" *Biochemistry* 40:675–682 (2001).

Kleiman et al., "Results From Late–Breaking Clinical Trials Sessions at ACCIS 2000 and ACC 2000" *Journal of the American College of Cardiology* 36(1):310–325 (Jul. 2000).

Levine et al., "Side Effects of Antithrombotic Therapy" *Hemostasis and Thrombosis: Basic Principles and Clinical Practice*, Third edition, Chapter 47, pp. 936–955 (1994).

Menon et al., "New Heparin Dosing Recommendations for Patients with Acute Coronary Syndrome" *The American Journal of Medicine* 110(8):641–650 (Jun. 2001).

Morrissey et al., "Resolution of Monomeric and Heterodimeric Forms of Tissue Factor, the High Affinity Cellular Receptor for Factor VII" *Thrombosis Research* 50:481–493 (1988).

Pitlick *Biochemistry* 10:2650–2657 (1971).

Refino et al., "A Human Antibody That Inhibits Factor IX/IXa Function Potently Inhibits Arterial Thrombosis Without Increasing Bleeding" *Arterioscler Thromb. Vasc. Biol.* 22:517–522 (Mar. 2002).

Refino et al., "Consequences of inhibition of plasma carboxypeptidase B on in vivo thrombolysis, thrombosis and hemostasis" *Fibrinolysis & Proteolysis* 14(5):305–314 (2000).

Refino et al., "Pharmacokinetics, Pharmacodynamics and Tolerability of a Potent, Non–peptidic, GP IIb/IIIa Receptor Antagonist following Multiple Oral Administrations of a Prodrug Form" *Thrombosis and Haemostasis* 79(1):169–176 (Jan. 1988).

Refino, "Addition of an Anti–Tissue Factor Antibody to a Sub–Optimal Heparin Regimen Increases Efficacy Without Further Compromise of Hemostasis in an Arterial Thrombosis Model" *Abstracts of XVIIth Congress of International Society of Thrombosis and Hemostasis Meeting, Paris, France, Jul. 6–12, 1997, published.*

Suggett et al., "Use of phage display for the generation of human antibodies that neutralize factor IXa function" *Blood Coagulation & Fibrinolysis* 11(1):27–42 (Jan. 2000).

Andrews et al., "Conservation of tissue factor primary sequence among three mammalian species" *Gene* 98:265–269 (1991).

Angal et al., "A single amino acid substitution abolishes the heterogeneity of chimeric mouse/human (IgG4) antibody" *Molecular Immunology* 30(1):105–108 (Jan. 1993).

Badimon et al., "Hirudin and Other Thrombin Inhibitors: Experimental Results and Potential Clinical Applications" *Trends Cardiovasc. Med.* 1(6):261–267 (1991).

Banner et al., "The crystal structure of the complex of blood coagulation factor VIIa with soluble tissue factor" *Nature* 380:41–46 (1996).

Bloom et al., "Intrachain disulfide bond in the core hinge region of human IgG4" *Protein Science* 6:407–415 (1997).

Bone, R. C., "Modulators of Coagulation: A Critical Appraisal of Their Role in Sepsis" *Arch Intern Med* 152:1381–1389 (1992).

Bromberg et al., "Tissue factor promotes melanoma metastasis by a pathway independent of blood coagulation" *Proc. Natl. Acad. Sci. USA* 92:8205–8209 (Aug. 1995).

Carson and Brozna, "The role of tissue factor in the production of thrombin" *Blood. Coag. Fibrinol* 4:281–292 (1993).

Carter, P. et al., "Humanization of an anti–p185$^{HER2}$ antibody for human cancer therapy" *Proc. Natl. Acad. Sci.* 89:4285–4289 (1992).

Chothia, C. et al., "Conformations of immunoglobulin hypervariable regions" *Nature* 342(6252):877–883 (1989).

Colman, R. W., "The Role of Plasma Proteases In Septic Shock" *The New England J. of Med.* 320(18):1207–1209 (1989).

Creasey et al., "Tissue Factor Pathway Inhibitor Reduces Mortality from *Escherichia coli* Septic Shock" *J. Clin. Invest.* 91:2850–2860 (1993).

Davie et al., "The Coagulation Cascade: Initiation, Maintenance, and Regulation" *Biochemistry* 30(43):10363–10370 (1991).

Dickinson and Ruf, "Active Site Modification of Factor VIIa Affects Interactions of the Protease Domain with Tissue Factor" *Journal of Biological Chemistry* 272(32):19875–19879 (Aug. 1997).

Dickinson et al., "Identification of surface residues mediating tissue factor binding and catalytic function of the serine protease factor VIIa" *Proc. Natl. Acad. Sci USA* 93:14379–14384 (Dec. 1996).

Drake et al., "Functional Tissue Factor Is Entirely Cell Surface Expressed on Lipopolysaccharide–stimulated Human Blood Monocytes and a Constitutively Tissue Factor–producing Neoplastic Cell Line" *Journal of Cell Biology* 109:389–395 (Jul. 1989).

Eaton et al., "Construction and characterization of an active factor VIII variant lacking the central one–third of the molecule" *Biochemistry* 25:8343–8347 (1986).

Eigenbrot et al., "X–Ray Structures of the Antigen–Binding Domains From Three Variants of Humanized Anti–p185$^{HER2}$ Antibody 4D5 and Comparison With Molecular Modeling" *J. Mol. Biol.* 229:969–995 (1993).

Fisher et al., "Cloning and Expression of Human Tissue Factor cDNA" *Thrombosis Research* 48(1):89–99 (1987).

Gast A. and T.B. Tschopp, "Inhibition of extrinsic and intrinsic thrombin generation by a novel synthetic thrombin inhibitor (Ro 46–6240), recombinant hirudin and heparin in human plasma" *Blood Coag. Fibrinolysis* 6:533–560 (1995).

Gibbs et al., "Identification of the Factor VIIa Binding Site on Tissue Factor by Homologous Loop Swap and Alanine Scanning Mutagenesis" *Biochemistry* 33(47):14003–14010 (1994).

Golino et al., "Effects of tissue factor induced by oxygen free radicals on coronary flow during reperfusion" *Nature Medicine* 2:35–40 (Jan. 1996).

Harlos et al., "Crystal structure of the extracellular region of human tissue factor" *Nature* 370:662–666 (1994).

Hartzell et al., "A Growth Factor–Responsive Gene of Murine BALB/c 3T3 Cells Encodes a Protein Homologous to Human Tissue Factor" *Molecular & Cellular Biology* 9(6):2567–2573 (Jun. 1989).

Haskel et al., "Prevention of Arterial Reocclusion After Thrombolysis With Recombinant Lipoprotein–Associated Coagulation Inhibitor" *Circulation* 84(2):821–827 (1991).

Hilpert et al., "Design and Synthesis of Potent and Highly Selective Thrombin Inhibitors" *J. Med. Chem* 37:3889–3901 (1994).

Himber et al., "Dissociation of Antithrombotic Effect and Bleeding Time Prolongation in Rabbits by Inhibiting Tissue Factor Function" *Throm Haemostasis* 78:1142–1149 (1997).

Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

Huang et al., "Substrate Recognition by Tissue Factor–Factor VIIa" *Journal of Biological Chemistry* 271(36):21752–21757 (Sep. 1996).

Huang et al., "The Mechanism of an Inhibitory Antibody on TF–initiated Blood Coagulation Revealed by the Crystal Structure of Human Tissue Factor, Fab 5G9 and TF 5G9 Complex" *J. Mol. Biol.* 275:873–894 (1998).

Jang et al., "Antithrombotic Effect of a Monoclonal Antibody Against Tissue Factor in a Rabbit Model of Platelet–Mediated Arterial Thrombosis" *Arteriosclerosis and Thrombosis* 12(8):948–954 (Aug. 1992).

Kelley et al., "A Soluble Tissue Factor Mutant Is a Selective Anticoagulant and Antithrombotic Agent" *Blood* 89(9):3219–3227 (1997).

Kelley et al., "Analysis of the Factor VIIa Binding Site on Human Tissue Factor: Effects of Tissue Factor Mutations on the Kinetics and Thermodynamics of Binding" *Biochemistry* 34(33):10383–10392 (1995).

Kirchhofer et al., "Active Site–Blocked Factors VIIa and IXa Differentially Inhibit Fibrin Formation in a Human Ex Vivo Thrombosis Model" *Arterioscler. Thromb. Vasc. Biol.* 15(8):1098–1106 (Aug. 1995).

Kirchhofer et al., "Characterization of a Distinct Tissue Factor Region Important for Interaction with Substrates Factor X and Factor IX" *Thromb. Haemost. Suppl. 300* (abstract No. 943) (Aug. 1999).

Kirchhofer et al., "Endothelial Cells Stimulated with Tumor Necrosis Factor–α Expressing Varying Amounts of Tissue Factor Resulting in Inhomogenous Fibrin Deposition in a Native Blood Flow System" *J. Clin. Invest.* 93:2073–2083 (May 1994).

Kirchhofer et al., "The Tissue Factor Region That Interacts with Substrates Factor IX and Factor X" *Biochemistry* 39:7380–7387 (2000).

Lee et al., "A Novel Soluble Tissue Factor Variant with an Altered Factor VIIa Binding Interface" *Journal of Biological Chemistry* 273(7):4149–4154 (1998).

Levi et al., "Inhibition of Endotoxin–induced Activation of Coagulation and Fibrinolysis by Pentoxifylline or by a Monoclonal Anti–tissue Factor Antibody in Chimpanzees" *J. Clin. Invest.* 93:114–120 (Jan. 1994).

Martin et al., "Synthesis and Characterization of Wild–Type and Variant γ–Carboxyglutamic Acid–Containing Domains of Factor VII" *Biochemistry* 32:13949–13955 (1993).

McCallum et al., "Tissue Factor Positions and Maintains the Factor VIIa Active Site Far Above the Membrane Surface Even in the Absence of the Factor VIIa Gla Domain" *Journal of Biological Chemistry* 272:30160–30166 (Nov. 1997).

Mimms et al., "Phospholipid Vesicle Formation and Transmembrane Protein Incorporation Using Octyl Glucoside" *Biochemistry* 20(4):833–840 (1981).

Morrissey et al., "Molecular Cloning of the cDNA for Tissue Factor, the Cellular Receptor for the Initiation of the Coagulation Protease Cascade" *Cell* 50(1):129–135 (1987).

Morrissey et al., "Monoclonal Antibody Analysis of Purified and Cell–Associated Tissue Factor" *Thrombosis Research* 52:247–261 (1988).

Muller et al., "Structure of the Extracellular Domain of Human Tissue Factor: Location of the Factor VIIa Binding Site" *Biochemistry* 33(36):10864–10870 (1994).

Muller et al., "The Crystal Structure of the Extracellular Domain of Human Tissue Factor Refined to 1.7 A Resolution" *J. Mol. Biol.* 256:144–159 (1996).

O'Brien et al., "Factor VIII–Bypassing Activity of Bovine Tissue Factor Using the Canine Hemophilic Model" *J. Clin. Invest.* 82:206–211 (1988).

Paborsky et al., "Lipid Association, but Not the Transmembrane Domain, Is Required for Tissue Factor Activity" *Journal of Biological Chemistry* 266:21911–21916 (1991).

Paborsky et al., "Mammalian Cell Transient Expression of Tissue Factor for the Production of Antigen" *Protein Eng.* 3(6):547–553 (1990).

Paborsky et al., "Purification of Recombinant Human Tissue Factor" *Biochemistry* 28(20):8072–8077 (1989).

Pawashe et al., "A Monoclonal Antibody Against Rabbit Tissue Factor Inhibits Thrombus Formation in Stenotic Injured Rabbit Carotoid Arteries" *Circ. Res.* 74(1):56–63 (Jan. 1994).

Presta et al., "Humanization of an Anti–Vascular Endothelial Growth Factor Monoclonal Antibody for the Therapy of Solid Tumors and Other Disorders" *Cancer Research* 57(20):4593–4599 (Oct. 15, 1997).

Ragni et al., "Monoclonal Antibody Against Tissue Factor Shortens Tissue Plasminogen Activator Lysis Time and Prevents Reocclusion in a Rabbit Model of Carotid Artery Thrombosis" *Circulation* 93(10):1913–1918 (May 1996).

Rapaport and Rao, "Initiation and Regulation of Tissue Factor–Dependent Blood Coagulation" *Arterioscler. Thromb.* 12(10):1111–1121 (1992).

Rapaport and Rao, "The Tissue Factor Pathway: How It Has Become a "Prima Ballerina"" *Thrombosis and Haemostasis* 74:7–17 (1995).

Roy et al., "Lysine Residues 165 and 166 Are Essential for the Cofactor Function of Tissue Factor" *Journal of Biological Chemistry* 266(32):22063–22066 (Nov. 15, 1991).

Roy et al., "Self–association of Tissue Factor as Revealed by Chemical Cross–linking" *Journal of Biological Chemistry* 266(8):4665–4668 (1991).

Ruff et al., "Characterization of Factor VII Association with Tissue Factor in Solution" *The Journal of Biological Chemistry* 266(24):15719–15725 (Aug. 25, 1991).

Ruf et al., "Cofactor Residues Lysine 165 and 166 Are Critical for Protein Substrate Recognition by the Tissue Factor–Factor VIIa Protease Complex" *Journal of Biological Chemistry* 267(9):6375–6381 (Mar. 25, 1992).

Ruf et al., "Energetic Contributions and Topographical Organization of Ligand Binding Residues of Tissue Factor" *Biochemistry* 34:6310–6315 (1995).

Ruf et al., "Importance of Factor VIIa Gla–Domain Residue Arg–36 for Recognition of the Macromolecular Substrate Factor X Gla–Domain" *Biochemistry* 38:1957–1966 (1999).

Ruf et al., "Mutational Mapping of Functional Residues in Tissue Factor: Identification of Factor VII Recognition Determinants in Both Structural Modules of the Predicted Cytokine Receptor Homology Domain" *Biochemistry* 33(6):1565–1572 (1994).

Ruf et al., "Phospholipid–independent and –dependent Interactions Required for Tissue Factor Receptor and Cofactor Function" *Journal of Biological Chemistry* 266(4):2158–2166 (Feb. 5, 1991).

Ruf et al., "Purification, sequence and crystallization of an anti–tissue factor Fab and its use for the crystallization of tissue factor" *J. Crystal Growth* 122:253–264 (1992).

Ruf et al., "Tissue Factor Residues 157–167 Are Required for Efficient Proteolytic Activation of Factor X and Factor VII" *Journal of Biological Chemistry* 267(31):22206–22210 (Nov. 5, 1992).

Sakai et al., "Binding of Human Factors VII and VIIa to a Human Bladder Carcinoma Cell Line (J82)" *Journal of Biological Chemistry* 264(17):9980–9988 (Jun. 1989).

Shigematsu et al., "Expression of Human Soluble Tissue Factor in Yeast and Enzymatic Properties of Its Complex with Factor VIIa" *Journal of Biological Chemistry* 267(30):21329–21337 (Oct. 25, 1992).

Takayenoki et al., "cDNA and Amino Acid Sequences of Bovine Tissue Factor" *Biochem. & Biophys. Res. Comm.* 181:1145–1150 (Dec. 3, 1991).

Tanaka et al., "Purification of Glycosylated Apoprotein of Tissue Factor from Human Brain and Inhibition of Its Procoagulant Activity by a Specific Antibody" *Chemical Abstracts* (Abstract No. 49211z) 104:366 (1986).

Tanaka et al., "Purification of Glycosylated Apoprotein of Tissue Factor from Human Brain and Inhibition of its Procoagulant Activity by a Specific Antibody" *Thrombosis Research* 40:745–756 (1985).

Taylor, Jr. et al., "Lethal *E. coli* Septic Shock Is Prevented by Blocking Tissue Factor With Monoclonal Antibody" *Circ. Shock* 33(3):127–134 (Mar. 1991).

Thomas et al., "Tissue Factor Contributes to Microvascular Defects After Focal Cerebral Ischemia" *Stroke* 24:847–854 (1993).

Vaswani and Hamilton, "Humanized antibodies as potential therapeutic drugs" *Ann. Allergy Asthma Immunol.* 81:105–119 (Aug. 1998).

Vaughan et al., "Human antibodies by design" *Nature Biotechnology* 16:535–539 (Jun. 1998).

Warr et al., "Disseminated Intravascular Coagulation in Rabbits Induced by Administration of Endotoxin or Tissue Factor: Effect of Anti–Tissue Factor Antibodies and Measurement of Plasma Extrinsic Pathway Inhibitor Activity" *Blood* 75(7):1481–1489 (Apr. 1, 1990).

Waxman et al., "Human Factor VIIa and Its Complex with Soluble Tissue Factor: Evaluation of Asymmetry and Conformational Dynamics by Ultracentrifugation and Fluorescence Anisotropy Decay Methods" *Biochemistry* 32:3005–3012 (1993).

Waxman et al., "Tissue Factor and Its Extracellular Soluble Domain: The Relationship between Intermolecular Association with Factor VIIa and Enzymatic Activity of the Complex" *Biochemistry* 31(16):3998–4003 (1992).

Wilcox et al., "Localization of Tissue Factor in the Normal Vessel Wall and in the Atherosclerotic Plaque" *Proc. Natl. Acad. Sci. USA* 86:2839–2843 (Apr. 1989).

Zhang et al., "Structure of the Extracellular Tissue Factor Complexed with Factor VIIa Inhibited with a BPTI Mutant" *J. Mol. Biol.* 285:2089–2104 (1999).

Kirchhofer and Banner., "Molecular and Structural Advances in Tissue Factor–Dependent Coagulation." *Elsevier Science* (Trends in Cardiovascular) 7(8):316–324 (Nov. 1997).

Kirchhofer et al., "Anticoagulant Activity of Different Tissue Factor/Factor VIIa Inhibitors in a Human Ex–Vivo Thrombosis Model." *Blood* (suppl. 1) 86(10):91a (Nov. 15, 1995).

Kirchhofer et al., "Epitope Location on Tissue Factor Determines the Anticoagulant Potency of Monoclonal Anti–Tissue Factor Antibodies." *Thrombosis and Haemostasis.* 84(6):1072–1081 (Dec. 2000).

Presta et al., "Generation of a Humanized, High Affinity Anti–Tissue Factor Antibody for Use as a Novel Antithrombotic Therapeutic." *Thrombosis and Haemostasis.* 85(3):379–389 (Mar. 2001).

Refino et al., "A Human Antibody That Binds to the γ–Carboxyglutamic Acid Domain of Factor IX is a Potent Antithrombotic In Vivo." *Thombosis and Haemostasis* 82(3):1188–1195 (Sep. 1999).

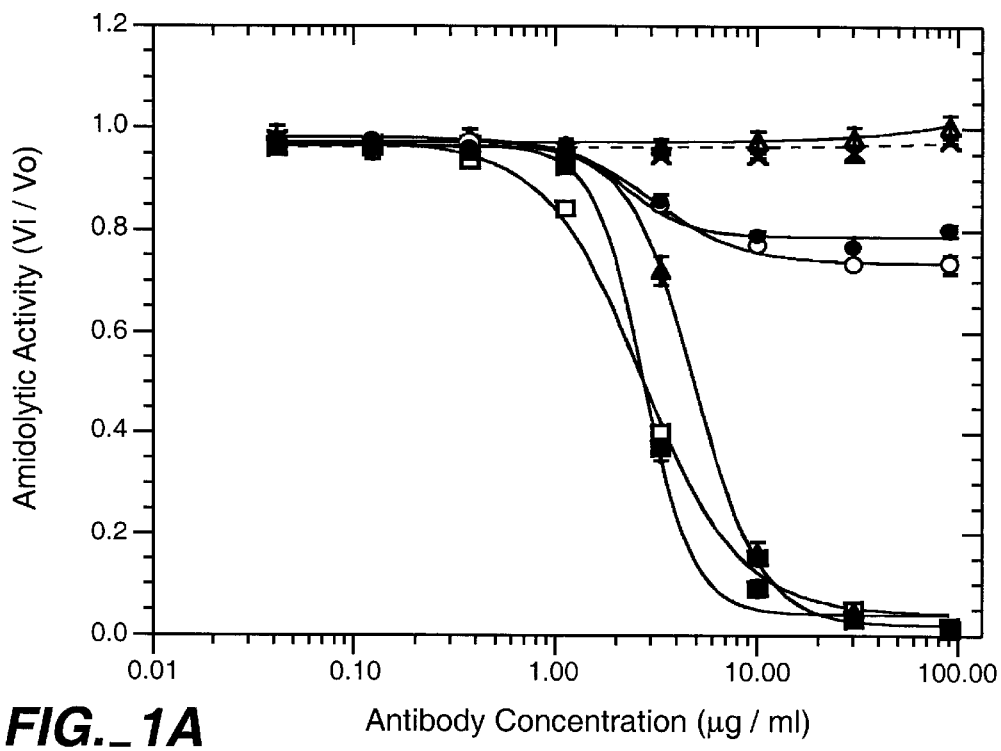
FIG._1A
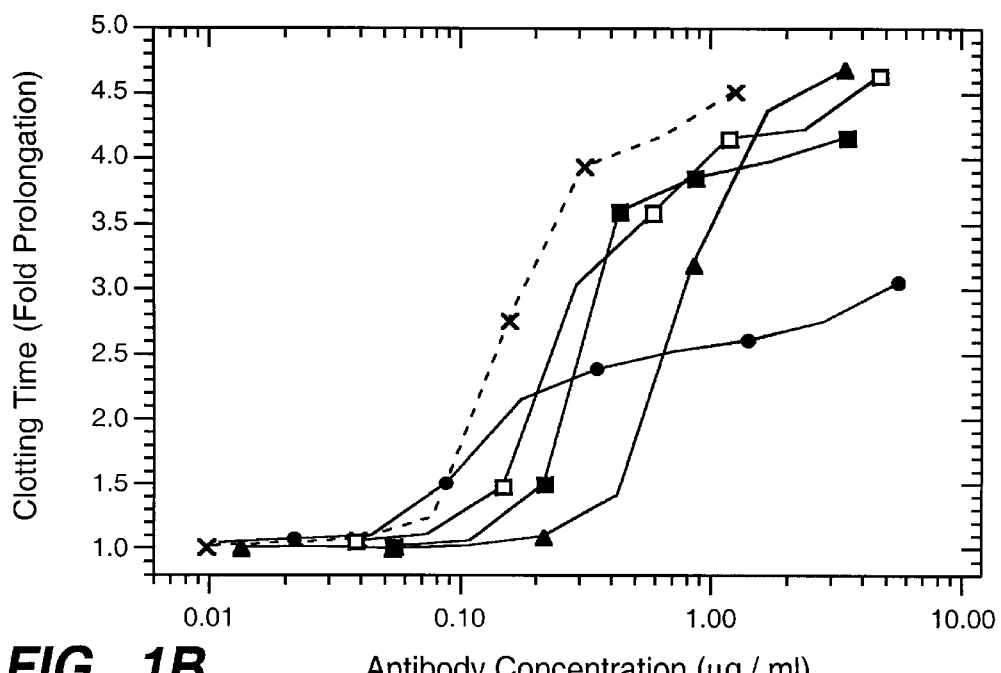
FIG._1B

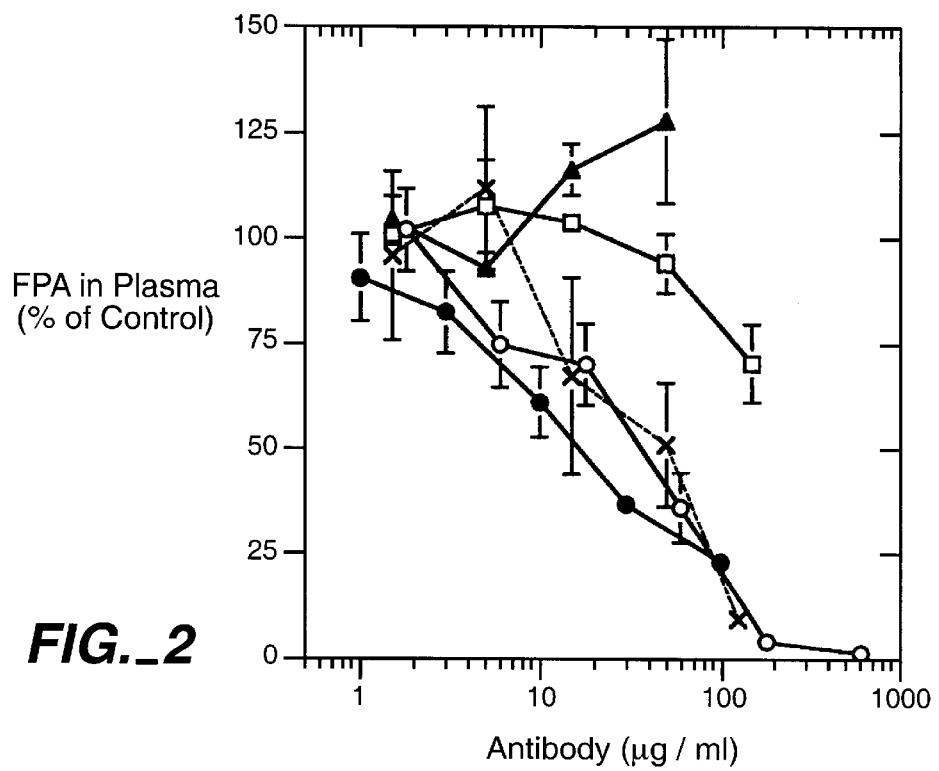
FIG._2
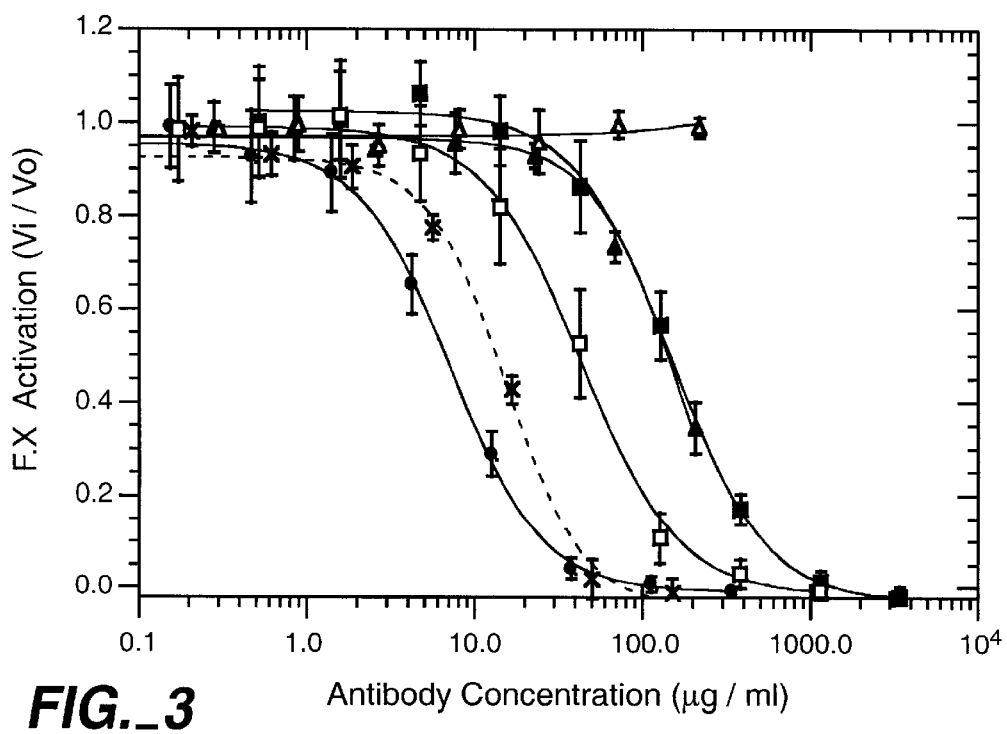
FIG._3

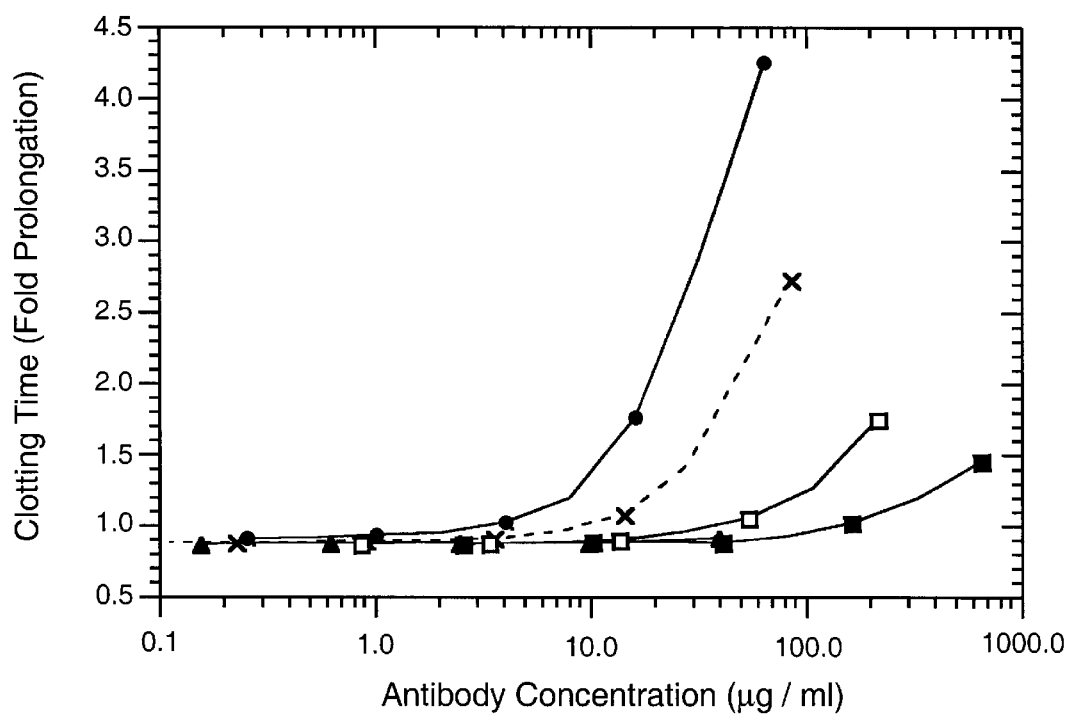
FIG._4

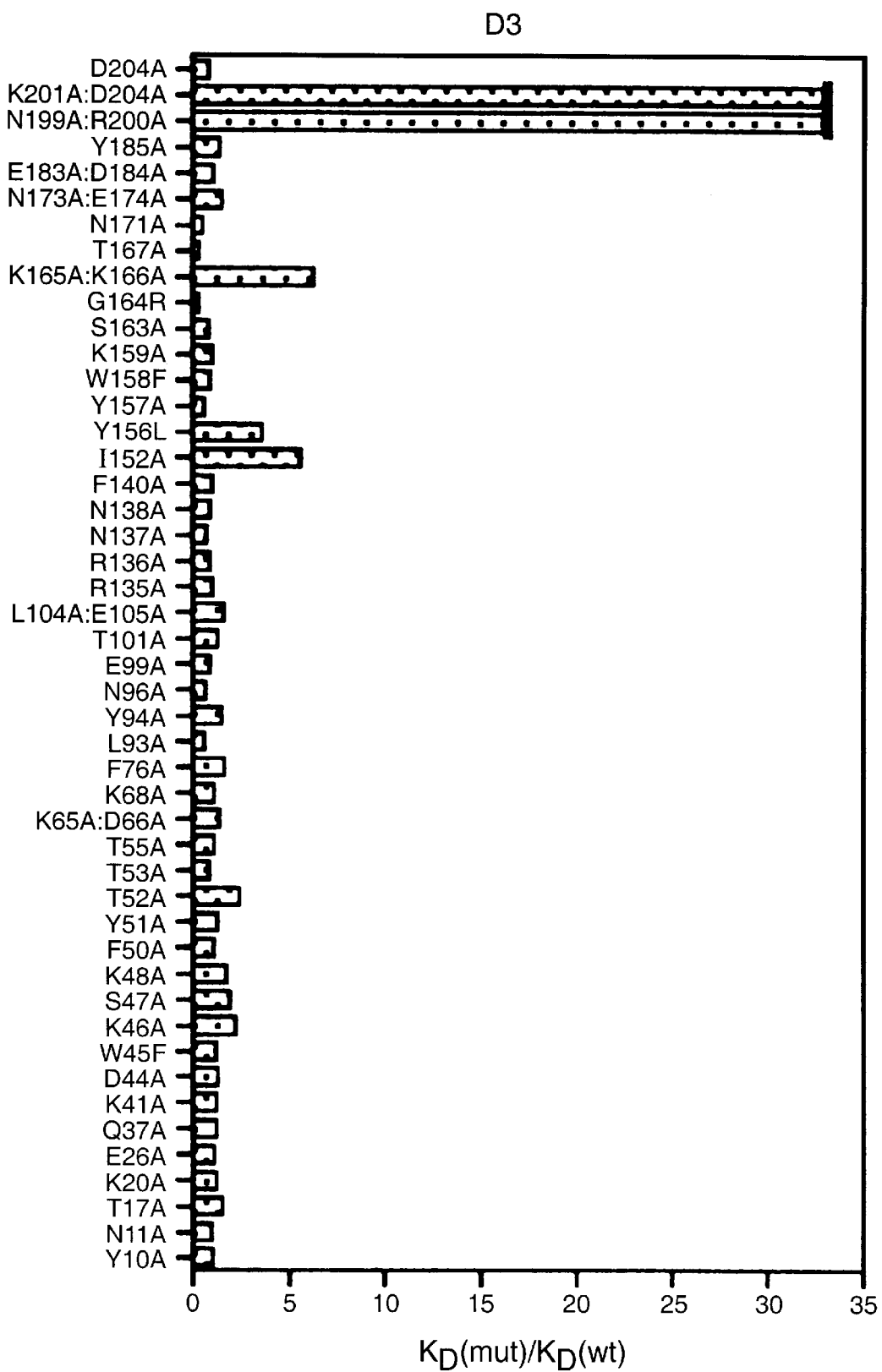
FIG._5A

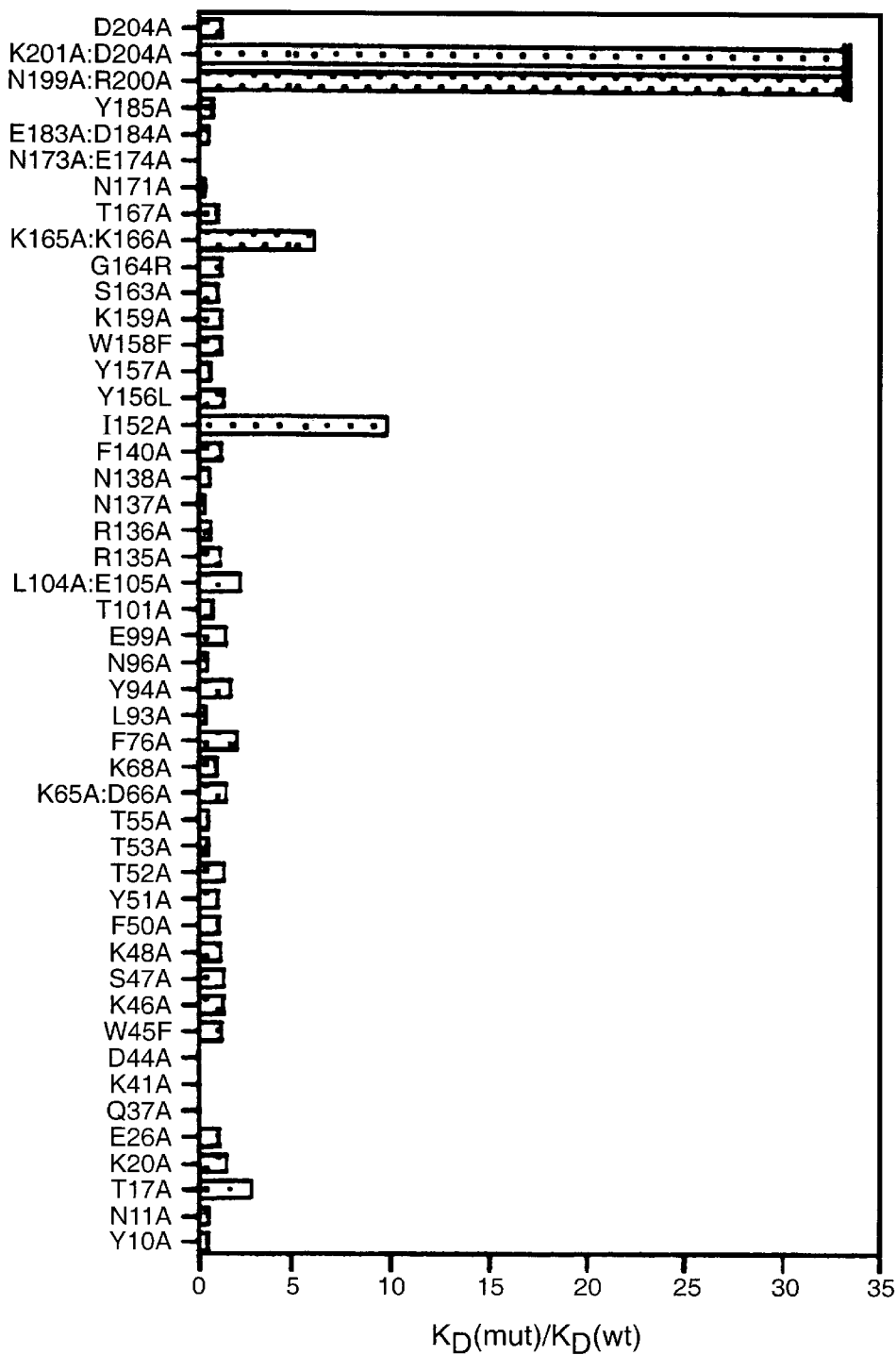
FIG._5B

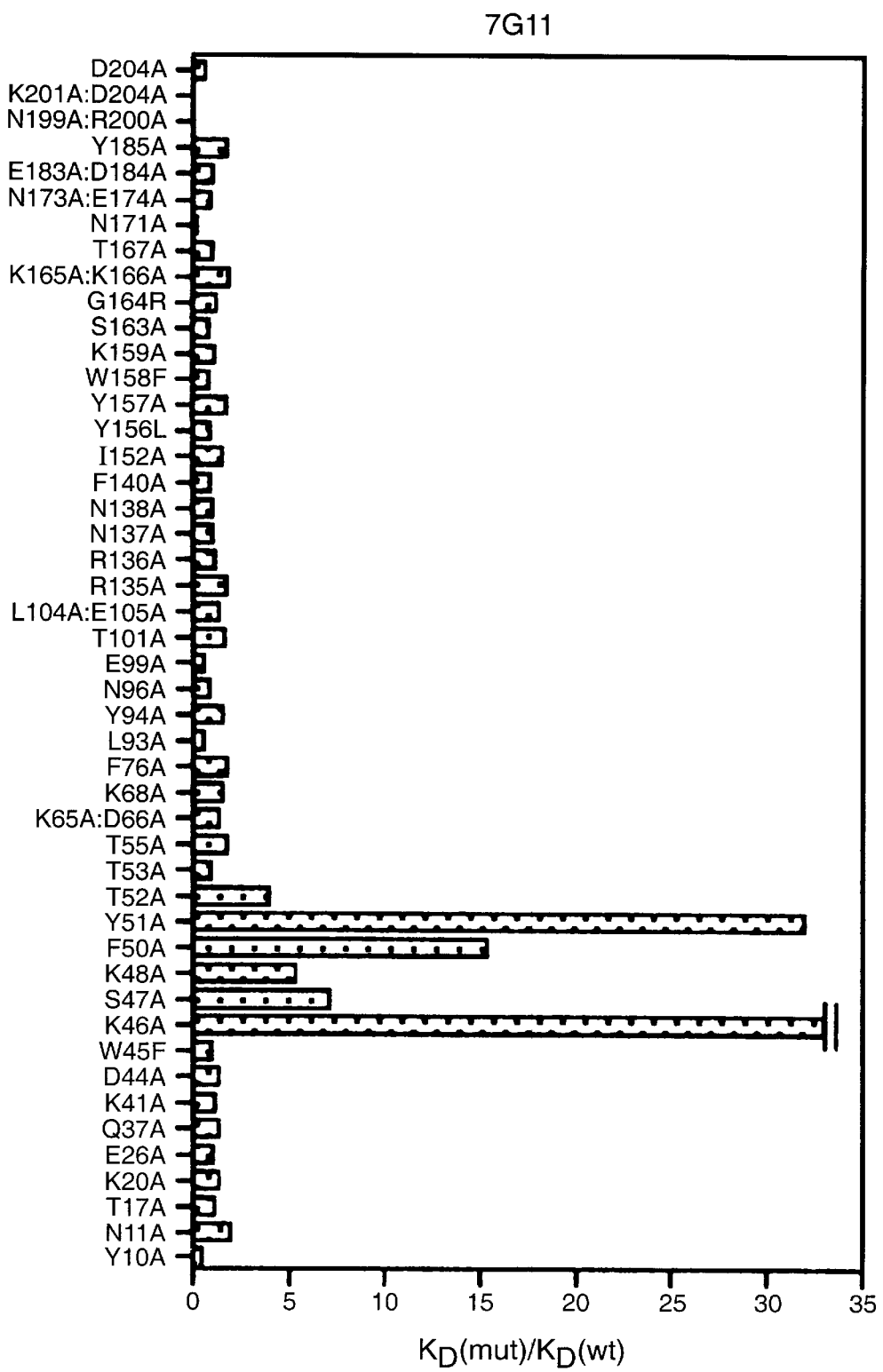
FIG._5C

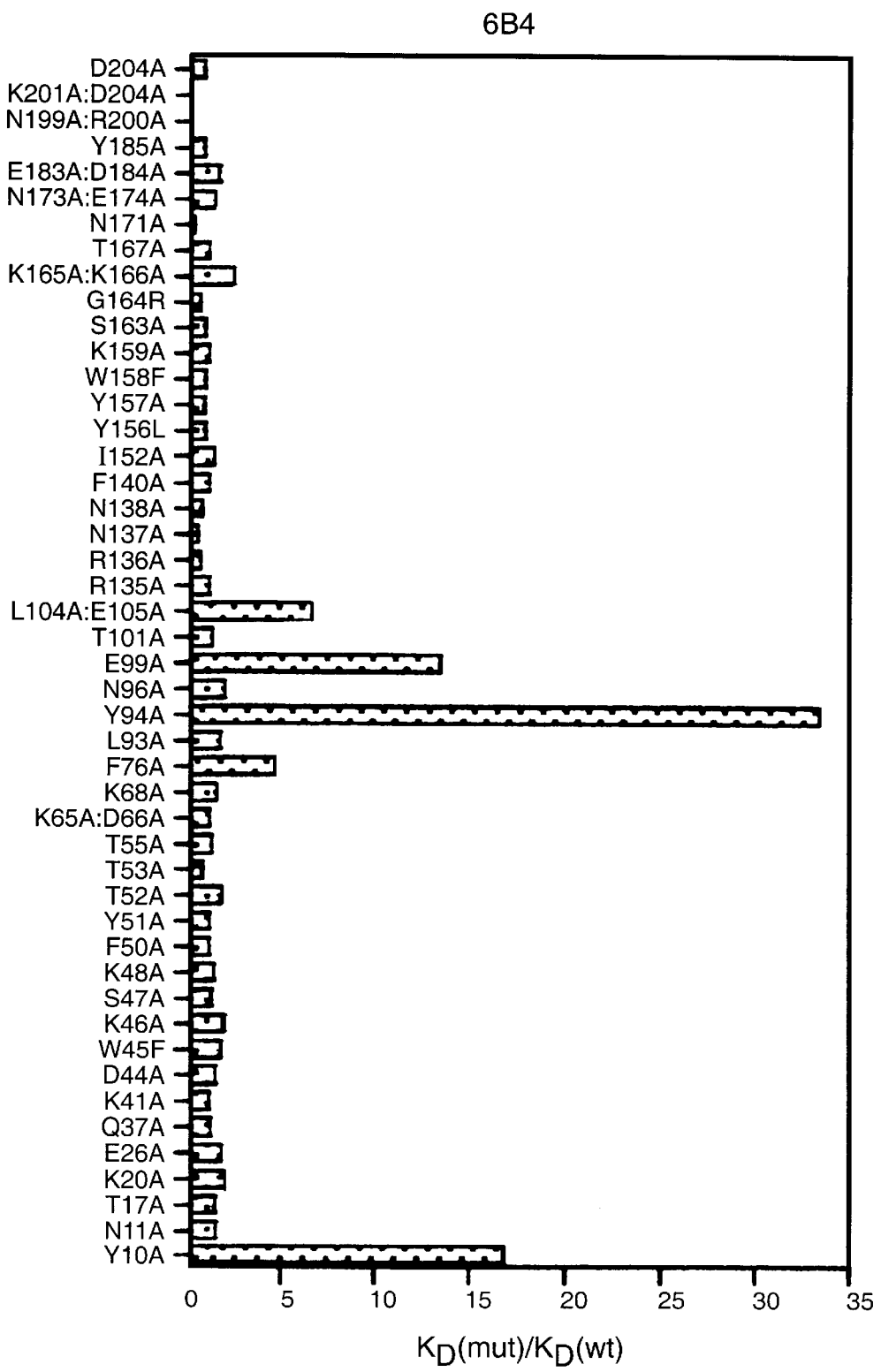
FIG._5D

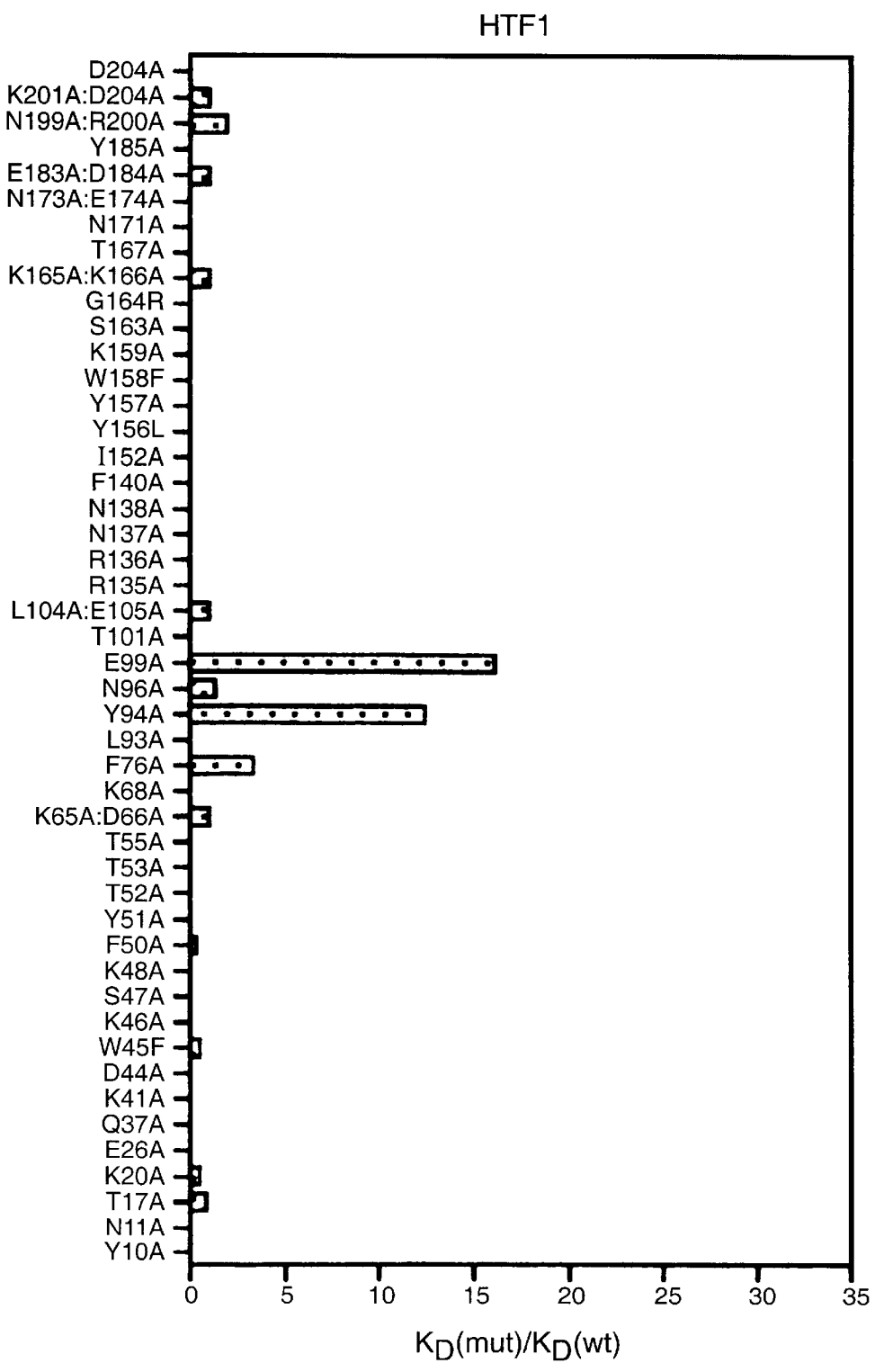
FIG._5E

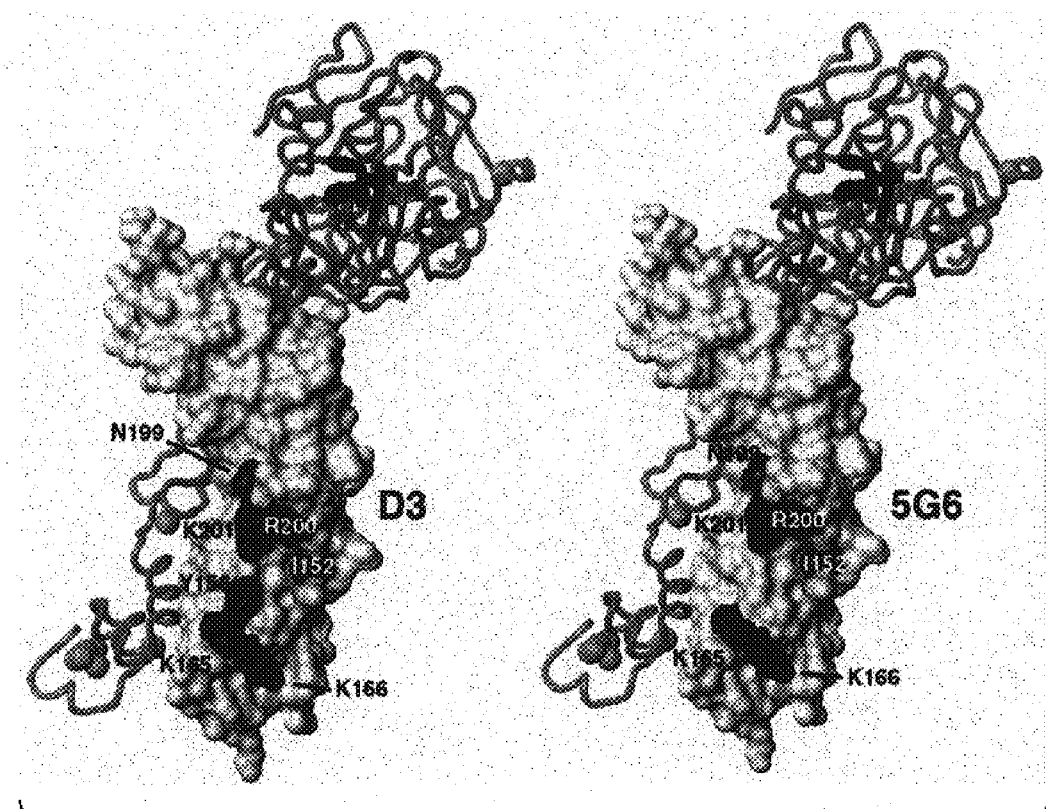
FIG._6A

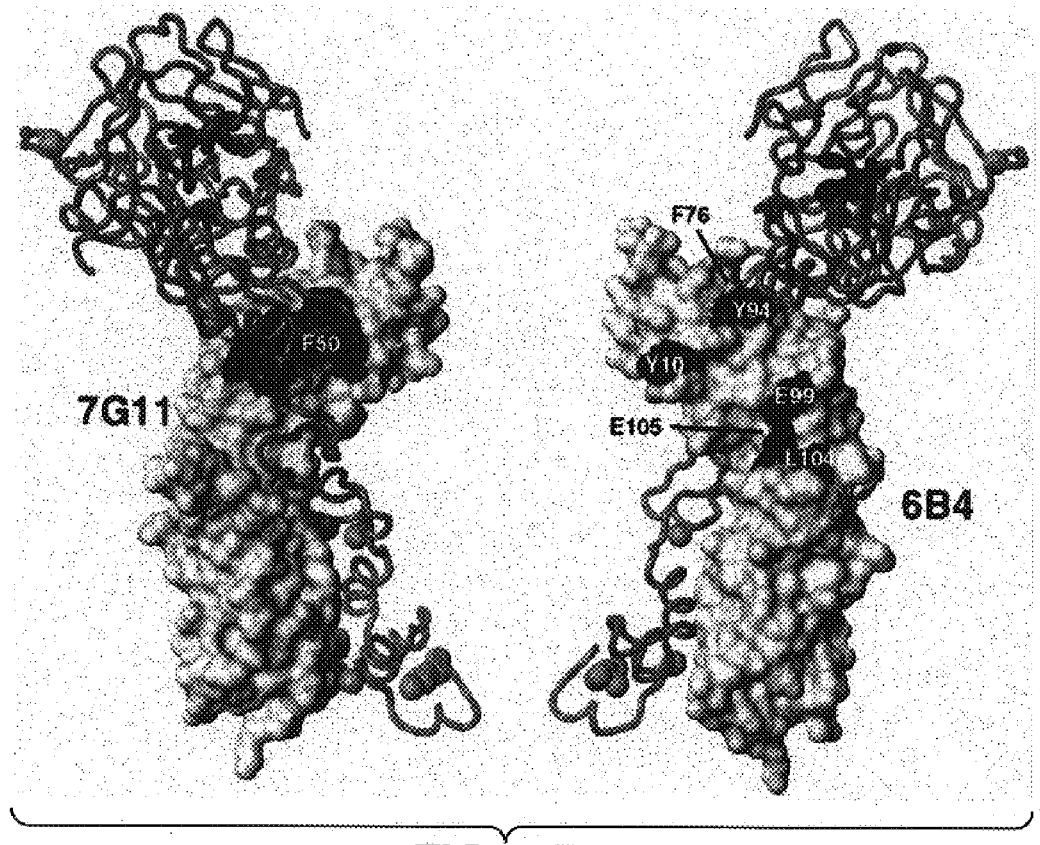
FIG._6B

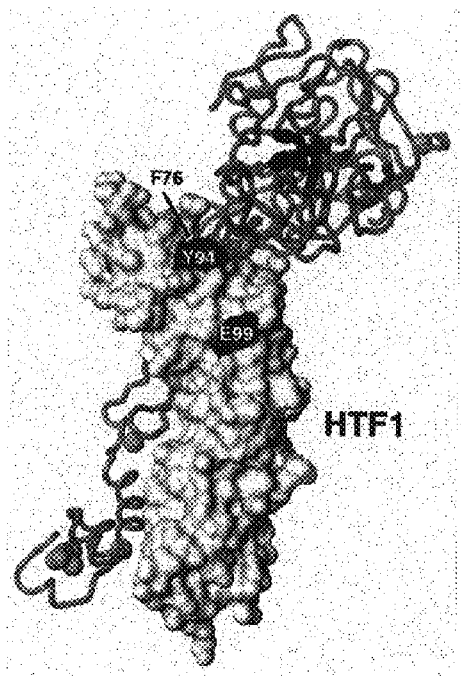
FIG._6C
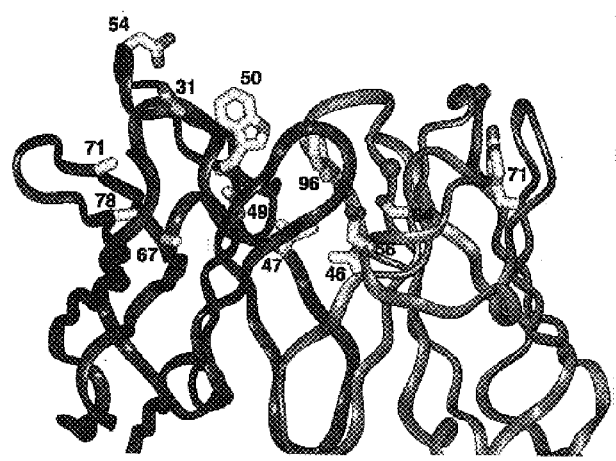
FIG._7

```
Variable Heavy
                     10         20         30         40
D3Mur        EVQLQQSGAELVRPGALVKLSCKASGFNIKDYYMHWVKQRPEQGLELIG
               **  **  *  ****    *        *      * * **    **
D3H44        EVQLVESGGGLVQPGGSLRLSCAASGFNIKEYYMHWVRQAPGKGLEWVG
                                     **** * *                  *
HumVHIII     EVQLVESGGGLVQPGGSLRLSCAASGFTFSSYAMSWVRQAPGKGLEWVA
                                       ----------
                                          CDR-H1

50   a    60         70         80  abc     90
D3Mur        WIDPENGNTIYDPKFQDKASITADTSSNTAYLQLSSLTSEDTAVYYCAR
              *     *           * *  * *       **   **
D3H44        LIDPEGNTIYDPKFQDRATISADNSKNTAYLQMNSLRAEDTAVYYCAR
             * ****  *  *   ****** *    *
HumVHIII     VISGDGGSTYYADSVKGRFTISRDNSKNTLYLQMNSLRAEDTAVYYCAR
             ------------------
                   CDR-H2

100        110
D3Mur        DTAAYFDYWGQGTTLTVSS    (SEQ ID NO: 1)
                              **
D3H44        DTAAYFDYWGQGTLVTVSS    (SEQ ID NO: 2)
             ******
HumVHIII     GRGGGSDYWGQGTLVTVSS
             --------
             CDR-H3                                  FIG._8

Variable Light
                    10         20         30         40
D3Mur        DIKMTQSPSSMSASLGESVTITCKASRDIKSYLSWYQQKPWKSPKTLIY
                *        *   * **       *        *        * *  *
D3H44        DIQMTQSPSSLSASVGDRVTITCRASRDIKSYLNWYQQKPGKAPKVLIY
                                       ** **   *               *
HumkI        DIQMTQSPSSLSASVGDRVTITCRAS-QISNYLAWYQQKPGKAPKLLIY
                                        -----------
                                            CDR-L1

50         60         70         80         90
D3Mur        YATSLADGVPSRFSGSGSGQDYSLTISSLESDDTATYYCLQHGESPFTFG
                  *                    * *    *** *             *
D3H44        YATSLAEGVPSRFSGSGSGTDYTLTISSLQPEDFATYYCLQHGESPWTFG
             * *  *                     *                   * ****
HumkI        AASSLESGVPSRFSGSGSGTDFTLTISSLQPEDFATYYCQQYNSLPWTFG
             -------                                      ---------
             CDR-L2                                          CDR-L3

100
D3Mur        SGTKLELKRT    (SEQ ID NO: 3)
              *  *  *
D3H44        QGTKVEIKRT    (SEQ ID NO: 4)

HumkI        QGTKVEIKRT                                  FIG._9
```

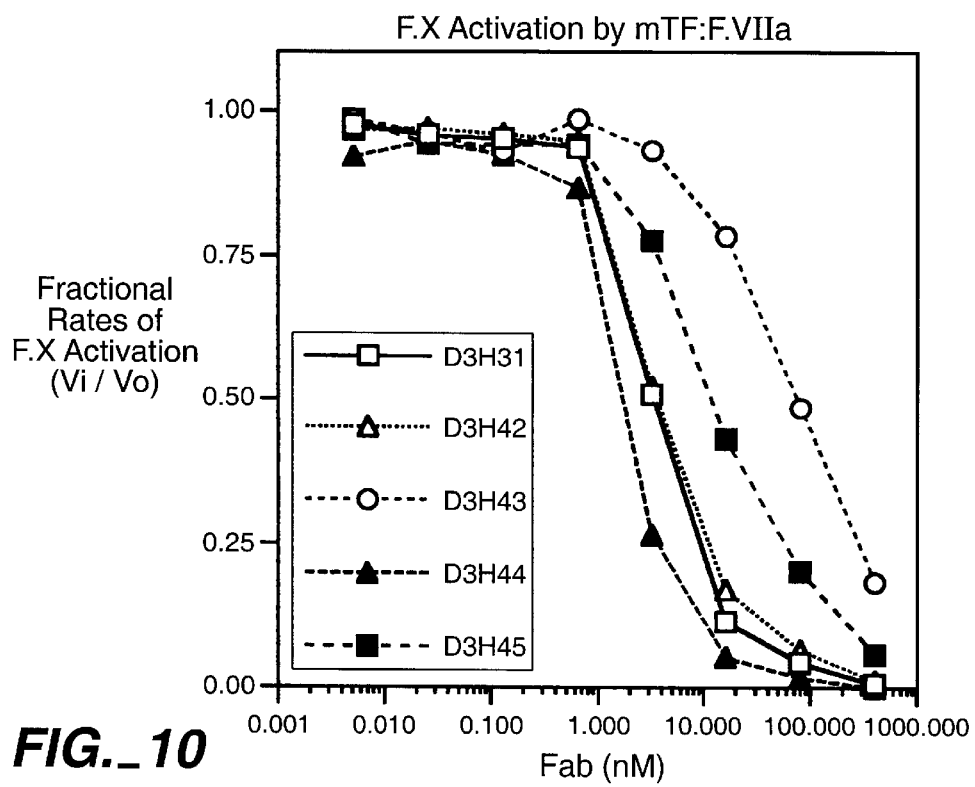
FIG._10
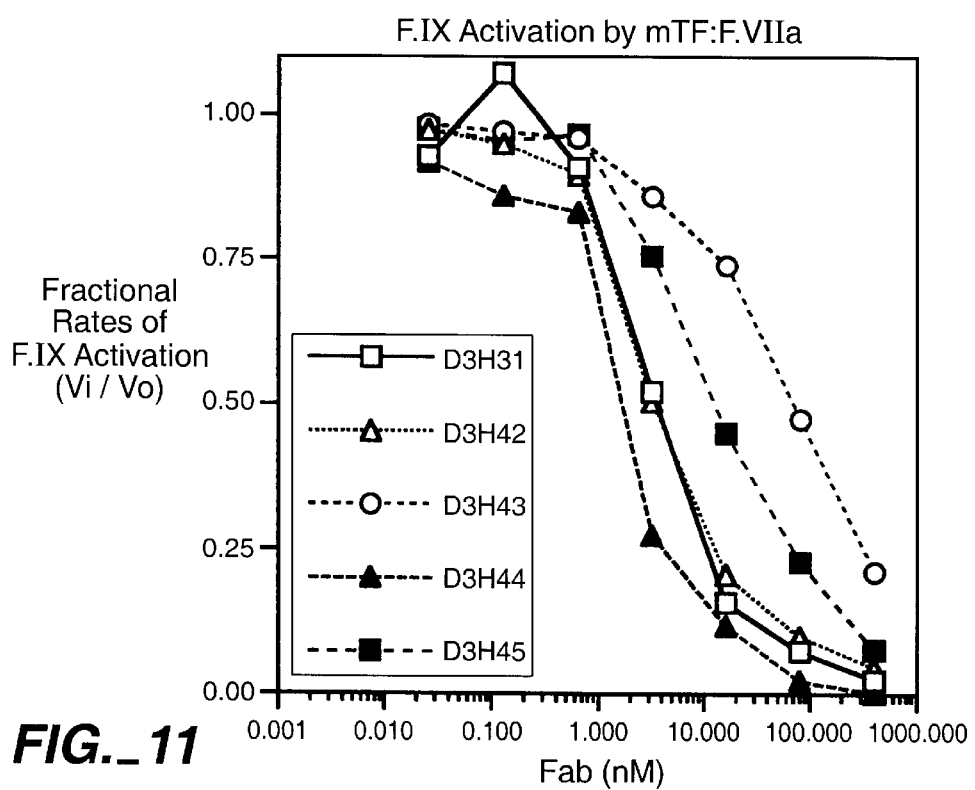
FIG._11

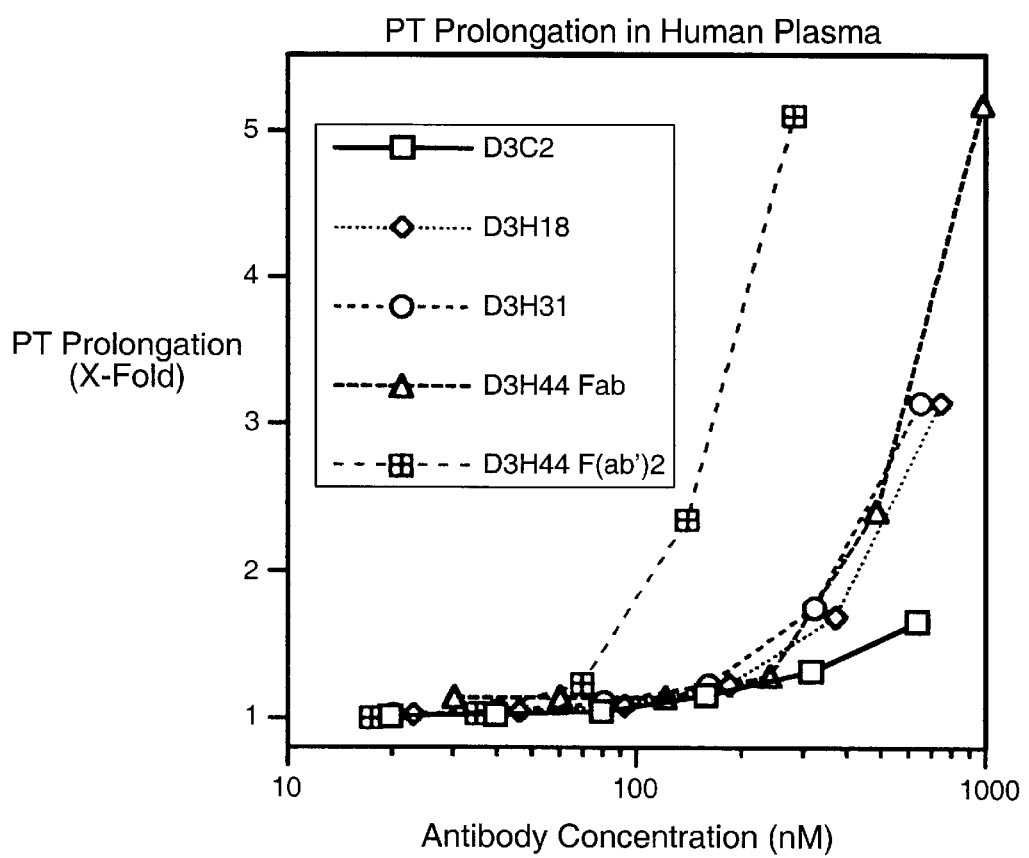
FIG._12

| | | | | | | | | | | | |
|---|---|---|---|---|---|---|---|---|---|---|---|
| Ser | Gly | Thr | Thr | Asn | Thr | Val | Ala | Ala | Tyr | Asn | Leu | Thr | Trp | Lys | Ser | Thr | Asn | Phe | Lys | Thr | Ile | 22 |
| Leu | Glu | Trp | Glu | Pro | Lys | Pro | Val | Asn | Gln | Val | Tyr | Thr | Val | Gln | Ile | Ser | Thr | Lys | Ser | Gly | Asp | 44 |
| Trp | Lys | Ser | Lys | Cys | Phe | Tyr | Thr | Thr | Asp | Thr | Glu | Cys | Asp | Leu | Thr | Asp | Glu | Ile | Val | Lys | Asp | 66 |
| Val | Lys | Gln | Thr | Tyr | Leu | Ala | Arg | Val | Phe | Ser | Tyr | Pro | Ala | Gly | Asn | Val | Glu | Ser | Thr | Gly | Ser | 88 |
| Ala | Gly | Glu | Pro | Leu | Tyr | Glu | Asn | Ser | Pro | Glu | Phe | Thr | Pro | Tyr | Leu | Glu | Thr | Asn | Leu | Gly | Gln | 110 |
| Pro | Thr | Ile | Gln | Ser | Phe | Glu | Gln | Val | Gly | Thr | Lys | Val | Asn | Val | Thr | Val | Glu | Asp | Glu | Arg | Thr | 132 |
| Leu | Val | Arg | Arg | Asn | Thr | Phe | Leu | Ser | Leu | Arg | Asp | Val | Phe | Gly | Lys | Asp | Leu | Ile | Tyr | Thr | 154 |
| Leu | Tyr | Tyr | Trp | Lys | Ser | Ser | Ser | Gly | Lys | Lys | Thr | Ala | Lys | Thr | Asn | Thr | Asn | Glu | Phe | Leu | 176 |
| Ile | Asp | Val | Asp | Lys | Gly | Glu | Asn | Tyr | Cys | Phe | Ser | Val | Gln | Ala | Val | Ile | Pro | Ser | Arg | Thr | Val | 198 |
| Asn | Arg | Lys | Ser | Thr | Asp | Ser | Pro | Val | Glu | Cys | Met | Gly | Gln | Glu | Lys | Gly | Glu | Phe | Arg | Glu | Ile | 220 |
| Phe | Tyr | Ile | Ile | Gly | Ala | Val | Val | Phe | Val | Val | Ile | Ile | Leu | Val | Ile | Ile | Leu | Ala | Ile | Ser | Leu | 242 |
| His | Lys | Cys | Arg | Lys | Ala | Gly | Val | Gly | Gln | Ser | Trp | Lys | Glu | Asn | Ser | Pro | Leu | Asn | Val | Ser | | 263 |

*FIG._13*

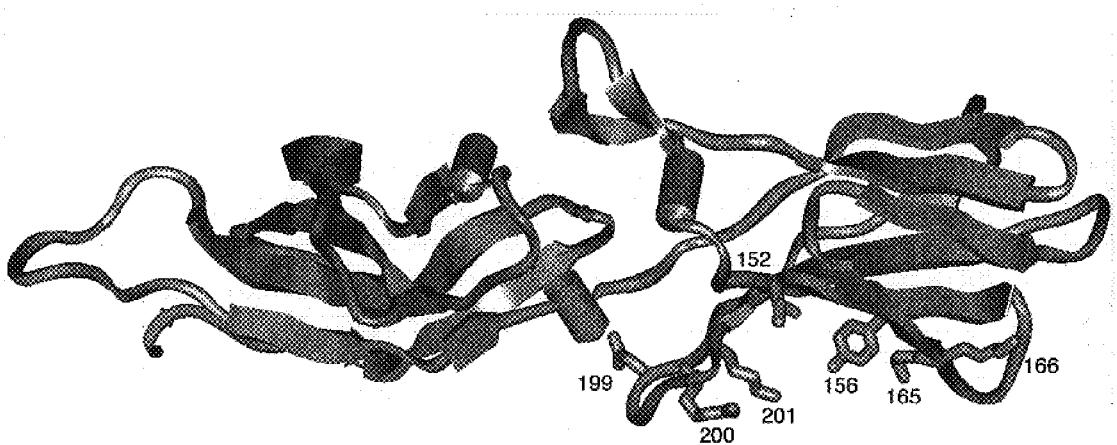
FIG._14

5G6 Heavy Chain
```
                10          20          30          40
5G6 VH   EVLLQQSGPELVKPGASVKIPCKASGYTFTEYNMDWVKQSHGKSLEWIG
                                    ----------
                                      CDR-H1

50   a     60          70          80  abc       90
5G6 VH   DINPNNGNTIYNQKFKGKATLTVDKSSTTAYLELRSLTSEDTAVYFCAR
         -----------------
             CDR-H2

100         110
5G6 VH   DHDYYFDFWGQGTTLTVSSA      (SEQ ID NO: 5)
         --------
          CDR-H3
```

5G6 Light Chain
```
                10          20          30          40
5G6 VL   DIQMTQTPASQSASLGESVTITCLASQTIDTWLAWYQQKPGKSPQLLIY
                                    -----------
                                       CDR-L1

50          60          70          80          90
5G6 VL   AATSLADGVPSRFSGSGSGTKFSFKISSLQAEDFVSYYCQQPYSSPYTF
         -------                                   ---------
         CDR-L2                                      CDR-L3

100
5G6 VL   GGGTKLELKRT      (SEQ ID NO: 6)
```

FIG._15

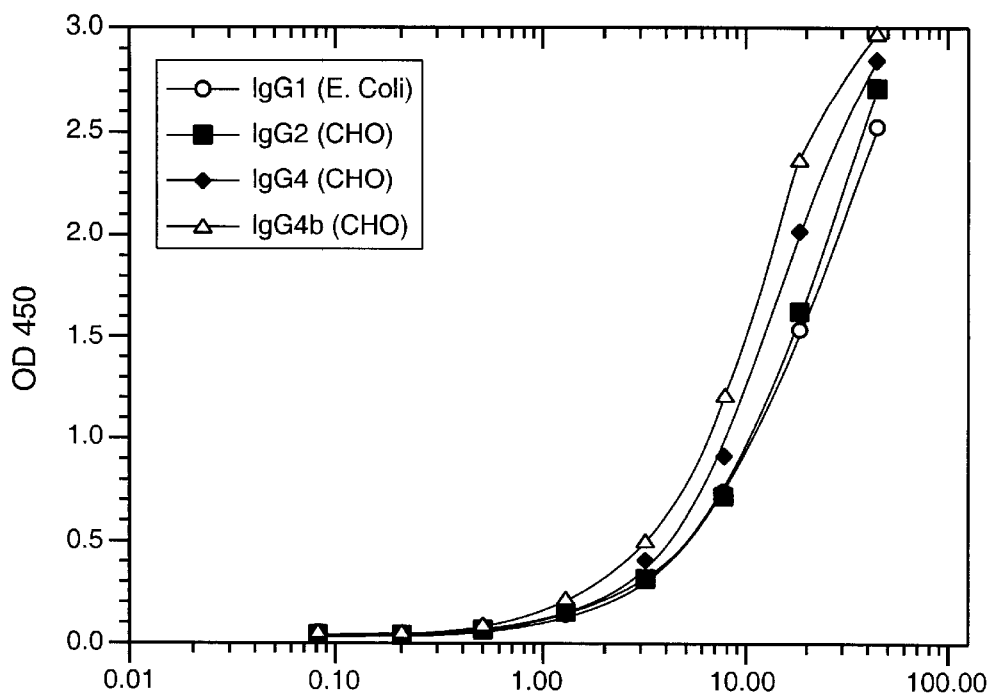
FIG._16
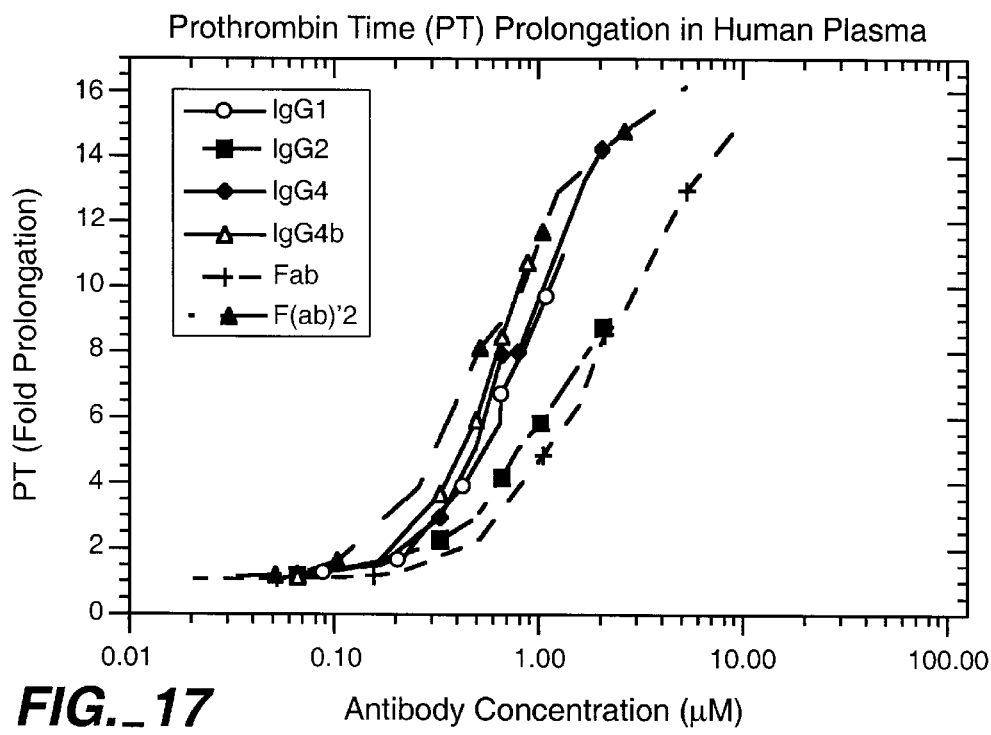
FIG._17

ANTI-TISSUE FACTOR ANTIBODIES WITH ENHANCED ANTICOAGULANT POTENCY

RELATED APPLICATIONS

This application is a non-provisional application filed under 37 CFR 1.53(b)(1), claiming priority under 35 USC 119(e) to provisional application No. 60/189,775 filed Mar. 16, 2000, the contents of which are incorporated herein by reference.

BACKGROUND OF THE INVENTION

1. Field of the Invention

This invention concerns methods for engineering anti-tissue factor (anti-TF) antibodies, especially those having enhanced anticoagulant potency. The invention further concerns anti-TF antibodies, methods and means for producing them, compositions comprising the antibodies and their use in the diagnosis, management, prevention and treatment of various diseases and disorders.

2. Description of the Related Art

A. Tissue Factor

Tissue factor (TF) is the receptor for coagulation factor VIIa (FVIIa) and the zymogen precursor factor VII (FVII). Native human TF (hTF) is a 263 amino acid residue glycoprotein composed of an extracellular domain (residues 1 to 219), a single transmembrane domain (residues 220–242), and a short cytoplasmic domain (residues 243 to 263) (Fisher et al., [1987] *Thromb. Res.* 48:89–99, Morrissey et al., [1987] *Cell* 50:129–135). The TF extracellular domain is composed of two immunoglobulin-like fibronectin type III domains of about 105 amino acids each (Huang et al., [1998] *J. Mol. Biol.* 275:873–894). Each domain is formed by two anti-parallel β-sheets with Ig superfamily type C2 homology.

The protein interaction of FVIIa with TF is mediated entirely by the TF extracellular domain (Muller et al., [1994] *Biochem.* 33:10864–10870; Gibbs et al., [1994] *Biochem.* 33:14003–14010; Ruf et al. [1994] *Biochem.* 33:1565–1572) which has been expressed in *E. coli*, cultured Chinese Hamster Ovary (CHO) cells and *Saccharomyces cerevisiae* (Waxman et al., [1992] *Biochemistry* 31:3998–4003; Ruf et al., [1991] *J. Bio. Chem.* 25 266:2158–2166 and Shigematsu et al., [1992] *J. Biol. Chem.* 267:21329–21337). The crystal structures of hTF extracellular domain and its complex with active site inhibited FVIIa have recently been determined by x-ray crystallography (Harlos et al., [1994] *Nature* 370:662–666; Muller et al., [1994] *Biochemistry* 33:10864; Muller et al., [1996] *J. Mol. Biol.* 256:144–159; Banner et al., [1996] *Nature* 380:41–46).

The hTF extracellular domain has also been extensively characterized by alanine scanning mutagenesis (Kelley et al., [1995] *Biochemistry,* 34:10383–10392; Gibbs et al., [1994] supra; Ruf et al., [1994] supra). Residues in the area of amino acids 16–26 and 129–147 contribute to the binding of FVIIa as well as the coagulant function of the molecule. Residues Lys20, Trp45, Asp58, Tyr94, and Phe140 make a large contribution (1 kcal/mol) to the free energy ($\Delta G$) of binding to FVIIa (Kelley et al., (1995) supra). Substitution of Lys20 and Asp58 with alanine residues leads to 78- and 30-fold reductions in FVIIa affinity respectively (Kelley et al., [1995] supra). A set of 17 single-site mutants at other nearby sites that are in contact with FVIIa result in modest decreases in affinity ($\Delta\Delta G$=0.3–1.0 kcal mol$^{-1}$). Mutations of TF residues Thr17, Arg131, Leu133 and Val207, each of which contact FVIIa in the crystal structure, have no effect on affinity for FVIIa. Lys15Ala and Tyr185Ala mutations result in small increases in affinity ($\Delta\Delta G$=−0.4 kcal mol$^{-1}$) (Kelley et al., [1995] supra). The 78-fold decrease in affinity imposed by the alanine substitution of Lys20 in hTF can be reversed by substituting a tryptophan for Asp58 (Lee and Kelley, [1998] *J. Biol. Chem.* 273:4149–4154).

Residues in the area of amino acids 157–168 contribute to the procoagulant function of TF-FVIIa (Kelley et al., [1995] supra; Ruf et al., [1992] *J. Biol. Chem.* 267:22206–22210) but are not important for FVII/FVIIa binding. It has been shown that lysine residues 165 and 166 are important to TF cofactor function but do not participate in FVIIa complex formation (Roy et al., [1991] *J. Biol. Chem.* 266:22063; Ruf et al., [1992] *J. Biol. Chem.* 267:6375). Lysine residues 165 and 166 are located on the C-terminal fibronectin type III domain of TF on the opposite surface of the molecule from residues found to be important for FVIIa binding on the basis of mutagenesis results (Kelley et al., (1995) supra). Alanine substitution of these lysine residues results in a decreased rate of FX activation catalyzed by the TF-FVIIa complex (Ruf et al., (1992) supra). The Lys165Ala-Lys166Ala variant (hTFAA) comprising residues 1–219 of hTF (sTF) inhibits the extrinsic pathway of blood coagulation in vitro through competition with membrane TF for binding to FVIIa. In a rabbit model of arterial thrombosis the variant partially blocks thrombus formation without increasing bleeding tendency (Kelley et al., (1997) Blood 89, 3219–3227). However, high doses of the variant are required for the antithrombotic effect, in part because FVIIa binds to cell surface TF approximately 1000-fold more tightly than to sTF (Kelley et al. (1997) supra). The greater apparent affinity is due to interaction of the FVIIa γ-carboxyglutamic acid-containing (Gla) domain with phospholipid.

TF is expressed constitutively on cells separated from plasma by the vascular endothelium (Carson, S. D. and J. P. Brozna, [1993] *Blood Coag. Fibrinol.* 4:281–292). Its expression on endothelial cells and monocytes is induced by exposure to inflammatory cytokines or bacterial lipopolysaccharide (Drake et al., [1989] *J. Cell Biol.* 109:389). Upon tissue injury, the exposed extracellular domain of TF forms a high affinity, calcium dependent complex with FVII. Once bound to TF, FVII can be activated by peptide bond cleavage to yield serine protease FVIIa. The enzyme that catalyzes this step in vivo has not been elucidated, but in vitro FXa, thrombin, TF-FVIIa and FIXa can catalyze this cleavage (Davie, et al., [1991] *Biochemistry* 30:10363–10370). FVIIa has only weak activity upon its physiological substrates FX and FIX whereas the TF-FVIIa complex rapidly activates FX and FIX.

The TF-FVIIa complex constitutes the primary initiator of the extrinsic pathway of blood coagulation (Carson, S. D. and Brozna, J. P., (1993) *Blood Coag. Fibrinol.* 4:281–292; Davie, E. W. et al., [1991] *Biochemistry* 30:10363–10370; Rapaport, S. I. and L. V. M. Rao, [1992] *Arterioscler. Thromb.* 12:1111–1121). The complex initiates the extrinsic pathway by activation of FX to Factor Xa (FXa), FIX to Factor IXa (FIXa), and additional FVII to FVIIa. The action of TF-FVIIa leads ultimately to the conversion of prothrombin to thrombin, which carries out many biological functions (Badimon, L. et al., [1991] *Trends Cardiovasc. Med.* 1:261–267). Among the most important functions of thrombin is the conversion of fibrinogen to fibrin, which polymerizes to form a clot.

The involvement of this plasma protease system has been suggested to play a significant role in a variety of clinical manifestations including arterial and venous thrombosis, septic shock, adult respiratory distress syndrome (ARDS), disseminated intravascular coagulation (DIC) and various other disease states (Haskel, E. J. et al., [1991] *Circulation* 84:821–827; Holst, J. et al., [1993] *Haemostasis* 23 (suppl. 1):112–117; Creasey, A. A. et al., [1993] *J. Clin. Invest.* 91:2850–2860; see also, Colman R. W. [1989] *N. Engl. J. Med* 320:1207–1209; Bone, R. C. [1992] *Arch. Intern. Med.* 152:1381–1389). Overexpression and/or aberrant utilization of TF has been linked to the pathophysiology of both thrombosis and sepsis (Taylor et al., [1991] *Circ. Shock* 33:127; Warr et al., [1990] *Blood* 75:1481; Pawashe et al., [1994] *Circ. Res.* 74:56). TF is expressed on cells found in the atherosclerotic plaque (Wilcox et al., [1989] *Proc. Natl. Acad. Sci. U.S.A.* 86:2839). Additionally, TF has been implicated in tumor metastasis (Bromberg et al., [1995] *Proc. Natl. Acad. Sci. USA*, 92:8205).

B. Anti-Tissue Factor Antibodies

Monoclonal antibodies in humanized or chimaeric forms are successfully used to treat a variety of diseases (Vaswani and Hamilton, [1998] *Ann. Allergy Asthma Immunol.* 81: 105–119; Vaughan et al., [1998] *Nature Biotechnology* 16: 535–539).

Antibodies reactive with hTF have been described (Tanaka et al., [1985] *Throm. Res.* 40:745–756; Tanaka et al., [1986] *Chem. Abstracts,* 104:366:4921 1z; Morrissey et al., [1988] *Throm. Res.* 52:247–260; U.S. Pat. No. 5,223, 427; Ruf et al., [1992] *J. Crystal Growth* 122:253–264; Huang et al., [1998] 275:873–894). Anti-TF monoclonal antibodies have been shown to inhibit tissue factor activity in various primate and non-primate species (Morrissey et al., [1988] supra; Huang et al. [1998] supra). Neutralizing anti-TF monoclona antibodies have been shown to prevent death in a baboon model of sepsis (Taylor et al., [1991] *Circ. Shock* 33:127), and attenuate endotoxin-induced DIC in rabbits (Warr et al., [1990], *Blood* 75:1481).

Inhibition of TF initiated blood coagulation by antibodies reactive with tissue factor has been proposed as a therapeutic modality (European Patent No. 0 266 993 B1), and the use of antibodies that specifically recognize TF at the site of thrombogenesis is currently viewed as a promising strategy for treating various thrombotic disorders. In fact, in vivo studies with anti-TF monoclonal antibodies demonstrated efficient anticoagulant activities (Levi et al., [1994] *J. Clin. Invest.* 93, 114–120; Taylor et al., [1991] *Circulatory Shock* 33, 127–134; Himber et al., [1997] *Thromb Haemostasis* 78, 1142–1149; Pawashe et al., [1994] *Circ. Res.* 74, 56–63; Ragni et al., [1996] *Circulation* 93, 1913–1918; Jang et al., [1992] *Arterioscl. Thromb.* 12, 948–954; Thomas et al., [1993] *Stroke* 24, 847–854; Golino et al., [1996] *Nature Med.* 2, 35–40). The use of a CDR-grafted anti-hTF antibody has been described for the attentuation or prevention of tissue factor mediated coagulation (International Publication No. WO 96/40921).

However, the precise TF binding sites of the antibodies used in the foregoing in vivo studies, with the exception of the antibody used by Levi et al., supra, are not known. The location of the antibody binding epitope may represent a critical factor in determining the inhibitory potencies of antibodies, because the cofactor function of TF involves several defined regions of the TF molecule. As a cofactor for factor VIIa (FVIIa), the cell surface exposed TF immobilizes FVII/FVIIa to the cell membrane thereby stabilizing the overall conformation of FVIIa (Waxman et al., [1993] *Biochemistry* 32, 3005–3012). The binding to TF also leads to the correct spatial orientation of the catalytic domain and the positioning of the active site in respect to the phospholipid membrane (McCallum et al., [1997] *J. Biol. Chem.* 272, 30160–30166; Banner et al., [1996] *Nature* 380, 41–46). Most of the TF-FVIIa contact surface area is provided by the FVIIa light chain interaction with TF. A smaller, yet critical contact surface lies between the N-terminal TF domain and the FVIIa catalytic domain. This contact is thought to play a main role in the enhancement of catalysis towards small synthetic as well as to macromolecular substrates (Dickinson et al., [1996] *Proc. Natl. Acad. Sci. USA* 93, 14379–14384; Dickinson and Ruf, [1997] *J. Biol. Chem.* 272, 19875–19879). In addition, TF participates in direct interaction with substrates (Huang et al., [1996] *J. Biol. Chem.* 271, 21752–21757) via residues K165 and K166 (Huang et al., supra; Ruf et al., [1992] *J. Biol. Chem.* 267, 6375–6381; Roy et al., [1991] *J. Biol. Chem.* 266, 22063–22066; Kelley et al., [1995] *Biochemistry* 34, 10383–10392), and neighboring residues (Ruf et al., [1992] *J. Biol. Chem.* 267: 22206–22210) in the C-terminal domain of TF. To add to this complex cofactor-enzyme-substrate interplay, recent observations suggested that the γ-carboxyglutamic acid-rich (Gla) domain of FVIIa contributes to substrate interaction (Huang et al., [1996] supra; Ruf et al., [1991] *J. Biol. Chem.* 266, 15719–15725; Martin et al., [1993] *Biochemistry* 32, 13949–13955; Ruf et al., [1999] *Biochemistry* 38, 1957–1966). Thus, anti-TF antibodies by virtue of their epitope location may interfere with one or several of these TF-mediated processes, which could translate into differences in their anticoagulant effectiveness. Such antibody epitope-dependent differences in potencies could be exacerbated under non-equilibrium conditions, which most likely prevail under therapeutic conditions. In this setting, antibody and the substrates circulating in blood would simultaneously interact with exposed TF.

In view of the limited characterization of most anti-TF antibodies known in the art, and the complexity of the mechanism by which TF exerts its thrombotic activity, it has so far been impossible to reliably engineer anti-TF antibodies with enhanced anticoagulant potency.

It is an objective of the present invention to determine which characteristics of anti-TF antibodies have the most profound effect on their anticoagulant properties. It is another objective, to design anti-TF antibodies with enhanced anticoagulant potency.

SUMMARY OF THE INVENTION

The present invention is based in part on the experimental finding that potency differences between various anti-TF antibodies can be explained by the location of the TF epitopes to which the antibodies bind and consequently, by the particular mode of inhibition. Anti-TF antibodies which bind to an epitope overlapping with the C-terminal macromolecular substrate-binding region of TF, and thus interfere with the TF-substrate interaction, are the most potent anticoagulant agents. This finding permits, for the first time, the purposeful design of anti-TF antibodies with high potency to treat or inhibit thrombosis.

Accordingly, one aspect of invention concerns a method for identifying anti-tissue factor (anti-TF) antibodies with enhanced anticoagulant potency, comprising (a) subjecting a plurality of anti-TF antibodies to epitope mapping, and (b) selecting antibodies binding to an epitope comprising at least part of the C-terminal macromolecular substrate-binding region of tissue factor (TF). The tissue factor is preferably human, and the macromolecular substrate preferably is Factor X (FX) or Factor IX (FIX). In a particularly preferred embodiment, the antibody selected recognizes an epitope which includes a TF region directly interacting with substrate factor FX or FIX, preferably by binding to a site which prevents or blocks association of TF with a Gla domain of the substrate factor. In another preferred embodiment, the antibody selected binds an epitope comprising residues K165, K166 and K201 of hTF. In yet another preferred embodiment, the epitope further comprises residues N199, R200 and I152 of hTF. In a further preferred embodiment, the epitope additionally comprises residue Y156 of hTF. In a particular embodiment, the method is used to identify antibodies that bind essentially to the same hTF epitope as any of antibodies D3, 5G6 and TF8-5G9. In some instances, it might be advantageous to select antibodies that have the binding properties specified above, and do not interfere with the association of hTF and Factor VIIa (FVIIa). All antibodies identified in accordance with the present invention may be poly- or monoclonal antibodies (as hereinafter defined), and may be rodent, (e.g. murine), humanized or human antibodies.

The invention also covers compositions comprising the antibodies identified in accordance with the present invention, and methods of using such antibodies to block a TF-FVIIa mediated or associated process or event, or to prevent or treat a TF-FVIIa related disease or disorder, including but not limited to, thrombotic and coagulopathic disorders.

In another aspect, the invention concerns a method for producing an antibody having enhanced anticoagulant potency, comprising raising antibodies against an antigen comprising at least part of the C-terminal macromolecular substrate binding region of tissue factor (TF). Again, the antibodies may be poly- or monoclonal antibodies (as hereinafter defined), including rodent, e.g. murine, humanized and human antibodies. In a preferred embodiment, the antibodies are raised against an antigen comprising the entire C-terminal macromolecular substrate-binding region of TF, preferably human TF (hTF). Preferably, the antigen used to raise the antibodies comprises residues K165, K166 and K201, and optionally residues N199, R200 and I152 o hTF. The antigen may additionally contain residue Y156 of hTF.

In yet another aspect, the invention concerns an anti-tissue factor (anti-TF) antibody heavy chain variable domain comprising the amino acid sequence of SEQ ID NO: 1 (VH SEQUENCE OF MURINE D3, FIG. 8) or SEQ ID NO: 2 (VH SEQUENCE OF HUMANIZED D3H44, FIG. 8).

In a further aspect, the invention concerns an anti-tissue factor (anti-TF) light chain variable domain comprising the amino acid sequence of SEQ ID NO: 3 (VL SEQUENCE OF MURINE D3, FIG. 9) or SEQ ID NO: 4 (VL SEQUENCE OF HUMANIZED D3H44, FIG. 9).

In a further aspect, the invention concerns an anti-tissue factor (anti-TF) heavy chain variable domain comprising the amino acid sequence of SEQ ID NO: 5 (VH SEQUENCE OF MURINE 5G6—FIG. 15).

In a different aspect, the invention concerns an anti-tissue factor (anti-TF) light chain variable domain comprising the amino acid sequence of SEQ ID NO: 6 (VL SEQUENCE OF MURINE 5G6—FIG. 15).

In another aspect, the invention concerns isolated nucleic acid comprising a sequence encoding an anti-tissue factor (anti-TF) antibody heavy chain variable domain of SEQ ID NO: 1, 2 or 5.

In yet another aspect, the invention concerns isolated nucleic acid comprising a sequence encoding an anti-tissue factor (anti-TF) antibody light chain variable domain of SEQ ID NO: 3, 4 or 6.

In a further aspect, the invention concerns a vector comprising, and capable of expressing, a nucleic acid as hereinabove defined, a recombinant host cell transformed with such vector, a cell culture comprising such recombinant host cell, and a method for expressing said nucleic acid to produce the encoded polypeptide.

The invention also concerns a humanized anti-tissue factor (anti-TF) antibody comprising a heavy and a light chain variable domain, wherein the heavy chain variable domain comprises hypervariable regions CDR-H1 having the sequence of GFNIKEYYMH (SEQ ID NO: 7), CDR-H2 having the sequence of LIDPEQGNTIYDPKFQD (SEQ ID NO: 8) and CDR-H3 having the sequence of DTAAYFDY (SEQ ID NO: 9). In a particular embodiment, the humanized anti-TF antibody of the present invention has a light chain variable domain comprising hypervariable regions CDR-L1 having the sequence of RASRDIKSYLN (SEQ ID NO: 10), CDR-L2 having the sequence of YATSLAE (SEQ ID NO: 11) and CDR-L3 having the sequence of LQHGESPWT (SEQ ID NO: 12). Preferably, both the heavy and light chain hypervariable regions are provided in a human framework region. Particular antibodies that are within the scope of the present invention include, without limitation: (a) murine antibody D3 (D3Mur), (b) humanized antibody D3H44, (c) murine antibody 5G6, and (d) antibodies specifically binding essentially the same epitope as any one of antibodies (a)–(c).

In another aspect, the invention concerns isolated nucleic acid comprising a sequence encoding a humanized anti-TF antibody heavy or light chain variable domain as hereinabove defined, a vector comprising and capable of expressing such nucleic acid, a recombinant host cell transformed with such vector, a cell culture comprising such recombinant host cell, and a method for expressing said nucleic acid to produce the encoded polypeptide.

In another aspect, the invention concerns a composition comprising an anti-tissue factor (anti-TF) antibody identifiable by the method of claim 1, in admixture with a pharmaceutically acceptable carrier. The antibody preferably is an anti-hTF antibody, and is preferably humanized or human. The composition may, for example, comprise an antibody selected from the group consisting of (a) murine antibody D3 (D3Mur), (b) humanized antibody D3H44, (c) murine antibody 5G6, and (d) an antibody specifically binding essentially the same epitope as any one of antibodies (a)–(c), in admixture with a pharmaceutically acceptable carrier.

The invention further concerns a method for the prevention or treatment of a TF-FVIIa related disease or disorder, such as thrombotic or coagulopathic disorder, comprising administering to a subject an effective amount of an anti-tissue factor (anti-TF) antibody of the present invention.

The invention also concerns diagnostic methods, diagnostic kits and articles of manufacture comprising one or more antibodies of the present invention, optionally in combination with one or more further active ingredients useful in the desired diagnostic or therapeutic application.

BRIEF DESCRIPTION OF THE DRAWINGS

FIG. 1 Inhibitory characteristics of anti-tissue factor antibodies. (a) Amidolytic activity of sTF:FVIIa towards the small synthetic substrate Chromozym t-PA. Antibodies were incubated together with sTF (10 nM) and FVIIa (10 nM) in HBS buffer, 5 mM $CaCl_2$ for 15 min. Chromozym t-PA (0.5 mM) was added and the rates of substrate cleavage were measured. The results were expressed in percent of control rates (average of 3 experiments±SD). (b) Prolongation of human plasma clotting by anti-TF antibodies. The antibodies were incubated with TF reagent (Innovin) for 15 min, then added to human citrated plasma. The increase in clotting times is reported as the ratio of clotting times in the presence of antibody and baseline values. The results are the average of two independent experiments. (filled circle) D3, (open circle) D3 Fab, (x) 5G6, (filled square) 7G11, (open square) 6B4, (filled triangle) HTF 1, (open triangle) isotype-matched control Ab.

FIG. 2 Inhibition of fibrinopeptide A (FPA) generation by anti-TF antibodies in a human ex-vivo blood flow system. The FPA concentrations in plasma are expressed in percent of control values. Each value is the average of 3–8 experiments except for the highest concentrations of D3 Fab and 5G6 (n=1 and n=2, resp.) and for two 6B4 concentrations (n=2 for 1.5 [g/ml and 15 µg/ml). The average of all control values (n=36) was 1348.6±46.1 ng/ml (±SEM). filled circle, D3; open circle, D3 Fab; x, 5G6; open square, 6B4; filled triangle, HTF1.

FIG. 3 Effects of anti-tissue factor antibodies on TF-dependent FX activation in human plasma. The inhibited rates of FXa generation during the initial phase of 45 sec were calculated and expressed as fractional activity (vi/vo). (filled circle) D3, (x) 5G6, (filled square) 7G11, (open square) 6B4, (filled triangle) HTF1, (open triangle) isotype-matched control Ab.

FIG. 4 Prolongation of prothrombin time (PT) by anti-tissue factor antibodies. Prolongation of clotting times are reported as the ratio of clotting times in the presence of antibody and baseline values. The results are the average of two independent experiments. (filled circle) D3, (x) 5G6, (filled square) 7G 11, (open square) 6B4, (filled triangle) HTF1.

FIG. 5 Effects of sTF mutations on antibody binding. The changes in binding affinities are expressed as the $K_D$ ratios of sTF mutants and sTF wildtype ($K_D$(mut)/$K_D$ (wt)). The $K_D$ values were calculated from surface plasmon resonance measurements with immobilized antibodies.

FIG. 6 Localization of the antibody epitopes on the crystal structure of the sTF:FVIIa complex. FVIIa is colored with the light chain in orange and the heavy chain in green. The active site inhibitor (D-Phe-L-Phe-Arg chloromethyl ketone) is in red and the calcium atoms in yellow. Tissue factor (grey) is in a solvent accessible representation and the antibody epitope residues are shown in red color. The figures were produced using Insight II (MSI, San Diego).

FIG. 7 Crystal structure of murine D3 F(ab). Ribbon diagram of VH (dark grey) and VL (light grey) backbones is shown. Side chains of residues changed or investigated during the humanization are shown and labeled; side chain nitrogens and oxygens are dark grey. Spheres represent two internal water molecules.

FIG. 8 Sequence alignment of VH domains of murine D3 (D3Mur), consensus human subgroup III (HumVHIII), and humanized D3H44. CDRs are underlined and differences between sequences are noted by *. CDR's are defined according to Kabar et al., Sequences of Proteins or Immunological Interest, 5$^{th}$ Ed. Public Health Service, National Institute of Health, Bethesda. Md.) (1991) except for CDR-H1 which was defined using a combination of CDR-H1 definitions from Kabat et al. (supra) and Chothia et al., Nature 342:877–883 (1989). i.e., CDR-H1 was defined as extending from residues H26–H35 in the heavy chain.

FIG. 9 Sequence alignment of VL domains of murine D3 (D3Mur), consensus human kappa subgroup I (HumκI), and humanized D3H44. CDRs are underlined and differences between sequences are noted by *. Residue numbering is according to Kabat et al. (1991), supra.

FIG. 10 Inhibition of the rate of FX activation by antibody F(ab) using membrane TF(mTF):FVIIa complex. The antibodies were incubated with mTF and FVIIa for 20 min before FX was added. Aliquots were taken at different time points and quenched in 20 mM EDTA. In the second stage of the assay, a chromogenic substrate S-2765 was added and the amidolytic activity measured at 405 nm on a kinetic microplate reader. The initial rates are calculated and the inhibition expressed as fractional rates (vi/vo) of FXa generation.

FIG. 11 Inhibition of the rate of F.IX activation by antibody F(ab) using membrane TF(mTF):FVIIa complex. The antibodies were incubated with mTF and FVIIa for 20 min before F.IX was added. Aliquots were taken at different time points and quenched in 30 mM EDTA-60% ethyleneglycol. In the second stage of the assay, a chromogenic substrate #299 was added and the amidolytic activity measured at 405 nm on a kinetic microplate reader. The initial rates are calculated and the inhibition expressed as fractional rates (vi/vo) of FIXa generation.

FIG. 12 Effects of antibody F(ab) and F(ab')$_2$ on prothrombin time (PT) in human plasma. E. coli expressed F(ab) of D3C2 (chimeric F(ab)), D3H18, D3H31, D3H44 and F(ab')$_2$ of D3H44 were incubated in human plasma for 5 min. Clotting was initiated by addition of human tissue factor reagent (Innovin). Clotting times were measured on an ACL 300 instrument. The prolongation of the clotting time is expressed as the ratio of inhibited clotting (with antibody) and uninhibited clotting time (buffer control). The indicated antibody concentrations are the concentrations in plasma.

FIG. 13 Amino acid sequence of human tissue factor (hTF) (SEQ ID NO: 13).

FIG. 14 Ribbon representation of the structure of the extracellular portion of human tissue factor.

FIG. 15 Heavy chain variable domain sequence of murine anti-TF antibody 5G6 (SEQ ID NO: 5). Light chain variable domain sequence of murine anti-TF antibody 5G6 (SEQ ID NO: 6).

FIG. 16 Binding of anti-tissue factor antibodies to tissue factor. IgG1, IgG2, IgG4 and IgG4b.

FIG. 17 Prolongation of human plasma clotting time (PT) for the full length versions and Fab and F(ab')$_2$ versions of D3H44.

DETAILED DESCRIPTION OF THE PREFERRED EMBODIMENTS

Definitions

Abbreviations used throughout the description include: FIXa for Factor IXa; FXIa for Factor XIa; FXa for Factor Xa; TF for tissue factor; FVII for zymogen factor VII; FVIIa for Factor VIIa; TF-FVIIa for tissue factor-Factor VIIa complex; FVII/FVIIa for FVII and/or FVIIa; sTF for soluble tissue factor composed of the extracellular domain residues 1–219 in the hTF sequence of FIG. 13 (SEQ ID NO: 13); hTFAA, the sTF variant containing Lys to Ala substitutions at positions 165 and 166 of the native hTF sequence; TF7I-C for the Kunitz type TF-FVIIa inhibitor of the same name in Dennis et al., (1994) J. Biol. Chem. 269(35):22129–22136; $K_D$ for equilibrium dissociation constant; PT for prothrombin time; APTT for activated partial thromboplastin time.

The term "anticoagulant potency" is used to refer to the ability of a substance, e.g. an antibody herein, to prevent, inhibit or prolong blood coagulation in an in vitro or in vivo assay of blood coagulation. Blood coagulation assays are known in the art and include, for example, prothrombin time assays such as those described in Example 1 herein, the human ex vivo thrombosis model described by Kirchhofer et al., *Arterioscler. Thromb. Vasc. Biol.* 15, 1098–1106 (1995); and Kirchhofer et al., *J. Clin. Invest.* 93, 2073–2083 (1994), and in the examples of the present application, and assays based on the measurement of Factor X activation in human plasma, as described in the examples of the present application.

The anticoagulant potency of an antibody of the present invention is "enhanced", if its ability to prevent, inhibit or prolong blood coagulation surpasses the ability of an anti-TF antibody that binds to a TF epitope other than an epitope comprising at least part of the C-terminal macromolecular substrate-binding region of TF, as determined in a standard in vivo or in vitro assay of blood coagulation, such as the assays referred to above. Preferably, the anti-TF with enhanced anticoagulant potency achieves the same effect (prevention, inhibition or prolongation) at a lower dose and/or in a shorter time than a reference antibody binding to a different TF epitope. Preferably, the difference between the potency of an antibody within the scope of the present invention and a reference antibody is at least about 1.5-fold, more preferably at least about 2-fold, even more preferably at least about 3-fold, most preferably at least about 5-fold, as determined by side-by-side comparison in a selected standard blood coagulation assay.

The "C-terminal macromolecular substrate-binding region of TF" is defined as the C-terminal region within the three-dimensional structure of TF that is responsible for the interaction of TF with its macromolecular substrate Factor X (FX) of Factor IX (FIX). In hTF, the FX interaction region is located within the second FNIII module of the extracellular domain of hTF as defined by Muller et al., *J. Mol. Biol.* 256, 144–159 (1996), including the β-strands $\beta 8_A$ to $\beta 16_G$ shown in FIG. 3 of Muller et al., supra, and in FIG. 14 herein. The main portion of the macromolecular substrate binding region of hTF includes residues Lys 165, Lys 166 (Roy et al., (1991) supra; Ruf et al., (1992) J. Biol. Chem.267:6375–6381; Huang et al., (1996) J. Biol. Chem. 271:21752–21757), Tyr 157, Lys 159, Ser 163, Gly 164, Tyr 185 (Kirchhofer et al., (1999) Thromb. Haemost. Suppl. 300, abstract; Kirchhofer et al., (2000) Biochemistry, 39:7380–7387). There are additional hTF residues which contribute to F.X interaction such as Tyr 156, Trp 158, Lys 169, Asn 173, Glu 174, Asn 199, Arg 200, Lys 201 and Asp 204. The substrate F.IX interacts with about the same hTF region, the main interaction region (Lys 165, Lys 166, Tyr 157, Lys 159, Ser 163, Gly 164, Tyr 185) being identical to that for F.X. The only difference observed concerned the hTF residues Trp 158 and Asp 204 both of which may be less important for F.IX interaction than for F.X interaction.

The term "epitope" is used to refer to binding sites for (monoclonal or polyclonal) antibodies on protein antigens.

Antibodies which bind to the C-terminal macromolecular substrate-binding region of TF are identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. Competition assays are discussed below. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

A "TF-FVIIa mediated or associated process or event", or equivalently, an "activity associated with plasma FVIIa", according to the present invention is any event which requires the presence of TF-FVIIa. The general mechanism of blood clot formation is reviewed by Ganong, in Review of Medical Physiology, 13th ed., Lange, Los Altos Calif., pp411–414 (1987) and Bach (1988) CRC Crit. Rev. Biochem. 23(4):359–368. Coagulation requires the confluence of two processes, the production of thrombin which induces platelet aggregation and the formation of fibrin which renders the platelet plug stable. The process comprises several stages each requiring the presence of discrete proenzymes and procofactors. The process ends in fibrin crosslinking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. Therefore, a process mediated by or associated with TF-FVIIa, or an activity associated with FVIIa includes any step in the coagulation cascade from the formation of the TF-FVII complex to the formation of a fibrin platelet clot and which initially requires the presence TF-FVIIa. For example, the TF-FVIIa complex initiates the extrinsic pathway by activation of FX to FXa, FIX to FIXa, and additional FVII to FVIIa. TF-FVIIa mediated or associated process, or FVIIa activity, can be conveniently measured employing standard assays such as those described in Roy, S., (1991) J. Biol. Chem. 266:4665–4668, and O'Brien, D., et al., (1988) J. Clin. Invest. 82:206–212 for the conversion of Factor X to Factor Xa in the presence of Factor VII and other necessary reagents.

A "TF-FVIIa related disease or disorder" is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC) and other diseases. The TF-FVIIa related disorder is not limited to in vivo coagulopathic disorders such as those named above but includes ex vivo TF-FVIIa related processes such as coagulation that may result from the extracorporeal circulation of blood, including blood removed in-line from a patient in such processes as dialysis procedures, blood filtration, or blood bypass during surgery.

"Bleeding disorders" are characterized by a tendency toward hemorrhage, both inherited and acquired. Examples of such bleeding disorders are deficiencies of factors VIII, IX, or XI. Examples of acquired disorders include acquired inhibitors to blood coagulation factors e.g., factor VIII, von Willebrand factor, factors IX, V, XI, XII and XIII, hemostatic disorders as a consequence of liver disease which included decreased synthesis of coagulation factors, bleeding tendency associated with acute and chronic renal disease and hemostasis after trauma or surgery.

The terms "tissue factor protein" and "mammalian tissue factor protein" are used to refer to a polypeptide having an amino acid sequence corresponding to a naturally occurring mammalian tissue factor or a recombinant tissue factor as described below. Naturally occurring TF includes human species as well as other animal species such as rabbit, rat, porcine, non human primate, equine, murine, and ovine tissue factor (see, for example, Hartzell et al., (1989) Mol. Cell. Biol., 9:2567–2573; Andrews et al., (1991) Gene, 98:265–269; and Takayenoki et al., (1991) Biochem. Biophys. Res. Comm., 181:1145–1150). The amino acid sequence of human tissue factor is shown in FIG. 13 (SEQ ID NO: 13). The amino acid sequence of the other mammalian tissue factor proteins are generally known or obtainable through conventional techniques.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Accordingly, "treatment" in the context of the present invention is an intervention performed with the intention of preventing a TF-FVIIa mediated or associated process or event, or a TF-FVIIa related disease or disorder, or a bleeding disorder, as hereinabove defined.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647–669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and binding site. This region consists of a dimer of one heavy chain and one light chain variable domain in tight, non-covalent association. It is in this configuration that the three hypervariable regions of each variable domain interact to define an antigen-binding site on the surface of the $V_H$–$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG 1, IgG2, IgG3, IgG4, IgA1, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624–628 (1991) and Marks et al., J. Mol. Biol. 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad Sci. USA 81:6851–6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522–525 (1986); Reichmann et al., Nature 332:323–329 (1988); and Presta, Curr. Op. Struct. Biol. 2:593–596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444–6448 (1993).

The expression "linear antibodies" when used throughout this application refers to the antibodies described in Zapata et al. *Protein Eng.* 8(10):1057–1062 (1995). Briefly, these antibodies comprise a pair of tandem Fd segments ($V_H$–$C_H$1–$V_H$–$C_H$1) which form a pair of antigen binding regions. Linear antibodies can be bispecific or monospecific.

METHODS FOR CARRYING OUT THE INVENTION

A. Antibody Preparation

Methods for humanizing nonhuman TF antibodies and generating variants of anti-TF antibodies are described in the examples below. In order to humanize an anti-TF antibody, the nonhuman antibody starting material is prepared. Where a variant is to be generated, the parent antibody is prepared. Exemplary techniques for generating such nonhuman antibody starting material and parent antibodies will be described in the following sections.

(i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

(ii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103, [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp.59–103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iii) Humanized Antibodies

Example 2 below describes procedures for humanization of an anti-TF antibody.

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody.

(iv) Amino Acid Sequence Variants of Antibodies

Example 2 also describes methodologies for generating amino acid sequence variants of an anti-TF antibody with enhanced affinity relative to the parent antibody.

Amino acid sequence variants of the anti-TF antibody are prepared by introducing appropriate nucleotide changes into the anti-TF antibody DNA, or by peptide synthesis. Such variants include, for example, deletions from, and/or insertions into and/or substitutions of, residues within the amino acid sequences of the anti-TF antibodies of the examples herein. Any combination of deletion, insertion, and substitution is made to arrive at the final construct, provided that the final construct possesses the desired characteristics. The amino acid changes also may alter post-translational processes of the humanized or variant anti-TF antibody, such as changing the number or position of glycosylation sites.

A useful method for identification of certain residues or regions of the anti-TF antibody that are preferred locations for mutagenesis is called "alanine scanning mutagenesis," as described by Cunningham and Wells *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with TF antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-TF antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-TF antibody with an N-terminal methionyl residue or the antibody fused to an epitope tag. Other insertional variants of the anti-TF antibody molecule include the fusion to the N- or C-terminus of the anti-TF antibody of an enzyme or a polypeptide which increases the serum half-life of the antibody (see below).

Another type of variant is an amino acid substitution variant. These variants have at least one amino acid residue in the anti-TF antibody molecule removed and a different residue inserted in its place. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |

TABLE 1-continued

| Original Residue | Exemplary Substitutions | Preferred Substitutions |
| --- | --- | --- |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-TF antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human TF. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. 0-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-TF antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TF antibody.

(v) Human Antibodies

Human antibodies can be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

(vi) Antibody Fragments

In certain embodiments, the humanized or variant anti-TF antibody is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107–117(1992) and Brennan et al., *Science* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology* 10:163–167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

(vii) Multispecific Antibodies

In some embodiments, it may be desirable to generate multispecific (e.g. bispecific) humanized or variant anti-TF antibodies having binding specificities for at least two different epitopes. Exemplary bispecific antibodies may bind to two different epitopes of the TF protein. Alternatively, an anti-TF arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the TF-expressing cell. Bispecific antibodies may also be used to localize cytotoxic agents to cells which express TF. These antibodies possess a TF-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

According to another approach for making bispecific antibodies, the interface between a pair of antibody 20 molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies, e.g. Shalaby et al., *J. Exp. Med.* 175:217–225 (1992).

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al.,*J. Immunol.* 152:5368 (1994). Alternatively, the bispecific antibody may be a "linear antibody" produced as described in Zapata et al. *Protein Eng.* 8(10):1057–1062 (1995).

Antibodies with more than two valencies are contemplated. For example, trispecific antibodies can be prepared. Tutt et al., *J. Immunol.* 147:60 (1991).

(viii) Other Modifications

Other modifications of the humanized or variant anti-TF antibody are contemplated. It may be desirable to modify the antibody of the invention with respect to effector function, so as to enhance the effectiveness of the antibody for instance in treating cancer. For example, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al., *Cancer Research* 53:2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, α-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-TF antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionuclide).

The anti-TF antibodies disclosed herein may also be formulated as immunoliposomes. Liposomes containing the antibody are prepared by methods known in the art, such as described in Epstein et al., *Proc Natl. Acad. Sci. USA* 82:3688 (1985); Hwang et al., *Proc. Natl Acad Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286–288 (1982) via a disulfide interchange reaction. A chemotherapeutic agent (such as Doxorubicin) is optionally contained within the liposome. See Gabizon et al., *J. National Cancer Inst.* 81(19):1484 (1989).

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328:457–458 (1987)). Antibody-abzyme conjugates can be prepared as described herein for delivery of the abzyme to a tumor cell population.

The enzymes of this invention can be covalently bound to the anti-TF antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604–608 [1984]).

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence: PKNSSMISNTP (SEQ ID NO: 14), and optionally further comprises a sequence selected from the group consisting of HQSLGTQ (SEQ ID NO: 15), HQNLSDGK (SEQ ID NO: 16), HQNISDGK (SEQ ID NO: 17), or VISSHLGQ (SEQ ID NO: 18), particularly where the antibody fragment is a Fab or F(ab')$_2$.

In another most preferred embodiment, the salvage receptor binding epitope is a polypeptide containing the sequence(s): HQNLSDGK (SEQ ID NO: 16), HQNISDGK (SEQ ID NO: 17), or VISSHLGQ (SEQ ID NO: 18) and the sequence: PKNSSMISNTP (SEQ ID NO: 14).

Covalent modifications of the humanized or variant anti-TF antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding the humanized or variant anti-TF antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa,* and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-TF antibody-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharonmyces pombe;* Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans,* and *K. marxianus; yarrowia* (EP 402,226); *Pichia pastoris* (EP 183,070); Candida; *Trichoderma reesia* (EP 244,234); *Neurospora crassa;* Schwanniomyces such as *Schwanniomyces occidentalis;* and filamentous fungi such as, e.g., Neurospora, Penicillium, Tolypocladium, and Aspergillus hosts such as *A. nidulans* and *A. niger.*

Suitable host cells for the expression of glycosylated anti-TF antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub et a., *Proc. Natl. Acad. Sci. USA* 77:4216 [1980]); mouse sertoli cells (TM4, Mather, *Biol. Reprod.* 23:243–251 [1980] kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 [1982]); MRC 5 cells; and FS4 cells.

Host cells are transformed with the above-described expression or cloning vectors for anti-TF antibody production and cultured in conventional nutrient media modified as appropriate for inducing promoters, selecting transformants, or amplifying the genes encoding the desired sequences.

The host cells used to produce the anti-TF antibody of this invention may be cultured in a variety of media. Commercially available media such as Ham's F10 (Sigma), Minimal Essential Medium ((MEM) (Sigma), RPMI-1640 (Sigma), and Dulbecco's Modified Eagle's Medium (DMEM) (Sigma) are suitable for culturing the host cells. In addition, any of the media described in Ham et al., *Meth. Enz.* 58:44 (1979), Barnes et al., *Anal. Biochem.*102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163–167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5–4.5, preferably performed at low salt concentrations (e.g.,from about 0–0.25M salt).

C. Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sci-*

*ences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other (see Section F below). Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody

The antibodies of the invention may be used as affinity purification agents. In this process, the antibodies are immobilized on a solid phase such as Sephadex resin or filter paper, using methods well known in the art. The immobilized antibody is contacted with a sample containing the TF protein (or fragment thereof) to be purified, and thereafter the support is washed with a suitable solvent that will remove substantially all the material in the sample except the TF protein, which is bound to the immobilized antibody. Finally, the support is washed with another suitable solvent, such as glycine buffer, pH 5.0, that will release the TF protein from the antibody.

Anti-TF antibodies may also be useful in diagnostic assays for TF protein, e.g., detecting its expression in specific cells, tissues, or serum. Such diagnostic methods may be useful in the diagnosis of various disorders associated with the aberrant expression, e.g. over- or underexpression of TF. For example, overexpression and/or aberrant utilization of TF has been linked to the pathophysiology of both thrombosis and sepsis, and TF has been implicated in tumor metastasis. Accordingly, anti-TF antibodies may be useful in the diagnosis of these diseases.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e g., anti-digoxin antibody). Thus, indirect conjugation of the label with the antibody can be achieved.

In another embodiment of the invention, the anti-TF antibody need not be labeled, and the presence thereof can be detected using a labeled antibody which binds to the TF antibody.

The antibodies of the present invention may be employed in any known assay method, such as competitive binding assays, direct and indirect sandwich assays, and immunoprecipitation assays. Zola, *Monoclonal Antibodies: A Manual of Techniques,* pp.147–158 (CRC Press, Inc. 1987).

Competitive binding assays rely on the ability of a labeled standard to compete with the test sample analyte for binding with a limited amount of antibody. The amount of TF protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g. U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the tumor immunoscintiography.

E. Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

For therapeutic applications, the anti-TF antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The antibodies also are suitably administered by intra tumoral, peritumoral, intralesional, or perilesional routes, to exert local as well as systemic therapeutic effects. The intraperitoneal route is expected to be particularly useful, for example, in the treatment of ovarian tumors.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

The anti-TF antibodies are useful in the treatment of various neoplastic and non-neoplastic diseases and disorders, such as TF-FVIIa related diseases or disorders. Such diseases or disorders include, for example, chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC). The TF-FVIIa related disorder is not limited to in vivo coagulopathic disorders such as those named above but includes ex vivo TF-FVIIa related processes such as coagulation that may result from the extracorporeal circulation of blood, including blood removed in-line from a patient in such processes as dialysis procedures, blood filtration, or blood bypass during surgery.

Depending on the type and severity of the disease, about 1 µg/kg to about 50 mg/kg (e.g., 0.1–20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the antibody in preventing or treating disease may be improved by administering the antibody serially or in combination with another agent that is effective for those purposes, such as commercially available forms of heparin, low molecular weight heparin and or inhibitors of platelet glycoprotein IIbIIIa, and or coumarin and or other anticoagulant or antiplatelet agents or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the antibody is suitably administered serially or in combination with radiological treatments, whether involving irradiation or administration of radioactive substances.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-TF antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may farther include other materials desirable from a commercial and user standpoint, including other buffers, diluents, filters, needles, syringes, and package inserts with instructions for use.

The following examples are offered by way of illustration and not by way of limitation. The disclosures of all citations in the specification are expressly incorporated herein by reference.

EXAMPLES

Example 1

This example describes the determination of the binding epitopes of 5 neutralizing anti-TF antibodies and establishes the respective roles of binding affinity and epitope location on the anticoagulant potencies in different systems. Interestingly, the results demonstrate that the anticoagulant potencies have no correlation with antibody binding affinities. Rather, potency is primarily determined by the precise location of the antibody-binding site on the TF molecules.

Materials and Methods

Materials

Fatty acid-free BSA was from Calbiochem (La Jolla, Calif.). Human recombinant FVIIa was a gift from Mark O'Connell (Genentech, Inc.). FX was from Haematologic Technologies Inc. (Essex Junction, Vt.). Thrombin inhibitor napsagatran was a gift from Dr. Kurt Hilpert (Roche, Switzerland). Chromozym t-PA was from Boehringer Mannheim (Indianapolis, Ind.). Truncated transmembrane tissue factor comprising residues 1–243 ($TF_{1-243}$) was generated and relipidated as described (47,48). FX chromogenic substrate S2765 was from Diapharma Group Inc. (Columbus, Ohio).

Preparation of Murine D3 Fab fragments

Fab fragments were prepared from the D3 antibody by digestion with papain in the presence of cysteine. A concentrated solution of the D3 Mab was prepared for digestion by dialysis versus 0.1 M sodium acetate pH 5.5, 1 mM EDTA. To this solution (11.6 mg/mL antibody) was added solid cysteine to a final concentration of 50 mM. Sufficient papain (Worthington Biochemical Corp., Lakewood, N.J.) was added to give a 1:100 weight ratio to antibody and the solution was incubated at 37° C. After 8 hours the digestion was quenched by addition of 100 mM iodoacetamide to inactivate the papain. Residual intact antibody and Fc fragments were removed by passing the solution over a Protein A-Sepharose column. The Fab fragments in the flow-through fraction were further purified by affinity chromatography on a column of immobilized soluble $TF_{1-219}$ (sTF). The affinity column was prepared by using a 1×5 mL NHS-activated HiTrap column (Pharmacia Biotech, Piscataway, N.J.) following the instructions supplied by the manufacturer. The final coupling density achieved was 25 mg of sTF per mL of resin. D3 Fab were eluted from this column by washing with a solution of 0.1 M acetate pH 3, 0.2 M NaCl and the Fab containing fractions were pooled and neutralized with 2 M Tris base.

Clotting Assays

For pre-incubation assays, 20 µl of antibody was added to 180 µl relipidated human tissue factor (Innovin, Dade Behring Inc., Newark, Del.) and incubated at 37° C. for 15 min. 100 µl of normal citrated human plasma (Peninsula Blood Bank, Burlingame, Calif.) was added and clotting times were measured using an MLA Electra 800 (Medical Laboratory Automation Inc.; Pleasant, N.Y.).

Prothrombin Time Assays

Prothrombin time (PT) assays, antibody was added to citrated human plasma. After 5 min incubation, clotting was started by adding human tissue factor reagent Innovin. Clotting times were measured on an ACL300 using the PT mode (Coulter Corp., Miami, Fla.). For both assays, the antibody concentrations are reported as final concentrations in the reaction mixture (including the tissue factor reagent).

Site-Directed Mutagenesis, Expression, and Purification of sTF Mutants

Expression of sTF mutants ($TF_{1-219}$) in *E. coli* and subsequent purification on a D3 antibody affinity column was carried out as described earlier (Kelley et al., [1995] Biochemistry 34: 10383–10392). For sTF mutants which did not bind to the D3 column (N199A:R200A and K201A:D204A), a 7G11 antibody column was used. This column was prepared by coupling the 7G 11 antibody to CNBr-activated Sepharose 4B (Pharmacia, Piscataway, N.J.) according to the manufacturer's instructions. Cell pellets were stored at −20° C. for at least 1 hr. The osmotic shock supernatants were applied to the antibody affinity column which was equilibrated with 50 mM Tris-HCl, pH 8.0, 500 mM NaCl (buffer A). To remove nonspecifically bound proteins, the column was washed with 6 column volumes of buffer A and 50 mM Tris-HCl pH 8.0, 1.0 M NaCl, 0.5M tetramethylamnmonium chloride. sTF mutants were eluted with 0.1 M sodium acetate, pH 3.0, 0.2 M NaCl. Fractions were neutralized and peak fractions concentrated using a Centriprep 10 (Amicon, Beverly, Mass.). Protein concentrations were determined by absorbance measurements using an $\lambda_{280}$ of 29.4 mM$^{-1}$ cm$^{-1}$ calculated from quantitative amino acid analysis data. An $\lambda_{280}$ of 24 mM$^{-1}$ cm$^{-1}$ was used for the Trp to Phe mutants of sTF.

Determination of Anti-TF Antibody's TF Binding Affinity and Antibody Epitope Mapping The binding affinity of sTF for immobilized antibody was determined by surface plasmon resonance (SPR) measurements on a Pharmacia BIAcore 2000 instrument (Pharmacia Biosensor). Each antibody was coupled to the sensor chip surface at a level of 2000–3000 resonance units using amine coupling chemistry (Pharmacia Biosensor). In a typical experiment, 4 different antibodies were immobilized on each of the 4 flow cells of the sensor chip so that sensorgrams could be recorded simultaneously for all 4 antibodies. Sensorgrams were recorded for sTF binding at concentrations ranging from 15.6 nM to 500 nM in 2-fold increments. The kinetic constants were determined by non-linear regression analysis according to a 1:1 binding model using software supplied by the manufacturer. Dissociation constants were calculated from the kinetic constants. In experiments to determine competition between the antibody and FVIIa for binding to sTF, the same sTF concentration series was prepared in the presence of 5 $\mu$M human, recombinant FVIIa. These solutions were incubated at ambient temperature for 30 minutes prior to injection onto the sensor chip. The epitopes on sTF for binding the monoclonal antibodies were determined by measuring the effect of amino acid substitutions in sTF on the affinity for immobilized antibody. Affinities were determined by SPR measurements as described above for the wild-type protein.

Monoclonal Antibodies

Monoclonal antibody 7G 11 was generated by immunizing female BALB/c mice subcutaneously 3 times, intraperitoneally 3 times with 20 $\mu$g sTF in MPL/TDM adjuvant (Ribi Immunochem Research, Hamilton, Mont.), at 2 week intervals. These mice were further boosted 8 times into footpads with 10 $\mu$g sTF in 100 ul MPL/TDM Adjuvant every week. 5G6 was generated by immunizing female BALB/c mice via footpad with 10 $\mu$g sTF in 100 ul MPL/TDM adjuvant, 13 times every week. Four days after the last boost, popliteal lymph nodes were removed and fused with mouse myeloma cells P3X63Ag8U.1 (Yelton et al., [1978] Curr. Top. Microbiol. Immunol. 81: 1–7) using 35% polyethyleneglycol as described (Chuntharapai and Kim, [1997] Methods Enzymol. 288: 15–27). Hybridoma cell lines secreting antibody specific for sTF, as determined by ELISA, were cloned twice by limiting dilution and further characterized. Ascites were produced in BALB/c mice and monoclonal antibodies were purified using protein G conjugated Sepharose 4B. The generation of D3 antibody was described previously (Paborsky et al., [1990] Prot. Engineering 3: 547–553) and the antibody 6B4 came from a separate immunization protocol. The HTF1 antibody was described by Carson et al. (Carson et al., [1987] supra).

FX Activation in Human Plasma

The antibodies were diluted in human citrated plasma from a donor plasma pool (Peninsula Blood Bank, Burlingame, Calif.) for 10 min at room temperature. At the end of the incubation period the thrombin inhibitor napsagatran (Hilpert et al., [1994] J. Med. Chem. 37: 3889–3901; Gast and Tschopp [1995] Blood Coag. Fibrinolysis 6: 533–560) was added. FX activation was started with relipidated TF$_{1-243}$ in 20 mM hepes, pH 7.5, 0.5% BSA (HBS buffer) containing 15 mM CaCl$_2$. The reaction mixture contained 33% plasma and the concentrations of relipidated TF$_{1-243}$, napsagatran and CaCl$_2$ were 0.4 nM, 0.5 $\mu$M and 5 mM, respectively. 50 $\mu$l aliquots taken at 15 sec intervals were quenched in 150 $\mu$l of 20 mM EDTA. In the second stage, 50 $\mu$l of 1.5 mM FXa chromogenic substrate S2765 was added and increase in absorbance at 405 nm monitored on a kinetic microplate reader (Molecular Devices, Menlo Park, Calif.). The initial rates were calculated by the linear fit of the values over a 45 sec. period. The values of aliquots taken at later time points indicated that the linear phase of the reaction was limited to this short time period. Control experiments in which relipidated TF$_{1-243}$ was omitted showed that there was no increase in chromogenic activity, indicating the absence of any FXa generation without TF. Also, napsagatran had no effect on FXa amidolytic activity towards S2765 under the employed conditions, which is consistent with the reported high selectivity towards thrombin (Hilpert et al., [1994] supra). From standard curves with FXa incubated with plasma and all other components used in the assay, it was calculated that under non-inhibited conditions an average of 8.6 nM±0.9 FXa/min (±S.D.) was generated.

The amidolytic activities of several coagulation factors, such as factors IIa, VIa, IXa and XIa were tested under identical assay conditions to test whether other coagulation factors generated during the reaction might have contributed to the amidolytic activity measured in the second stage of the assay. Only factor XIa displayed significant amidolytic activity towards S2765, which was about 25% of the FXa activity. To assess a possible contribution of factor XIa in our assay system, the inhibitory activity of the D3 antibody was examined in factor XI-deficient plasma (George King Bio-Medical, Overland Park, Kans.). The IC$_{50}$ value of 5.2±0.1 $\mu$g/ml (±SD, n=4) was similar to the value determined in normal human plasma. In addition, experiments carried out in factor II-, and factor VIII-deficient plasmas (American Diagnostica) gave similar results (6.4±0.9 $\mu$g/ml and 7.6±1.5 $\mu$g/ml respectively). Together, these results strongly suggested that rates of S2765 cleavage accurately reflected the concentration of FXa generated by relipidated TF$_{1-243}$:FVIIa complex in plasma.

Amidolytic Activity of Soluble TF:FVIIa Complex

The antibodies were incubated with sTF and FVIIa in HBS buffer containing 5 mM CaCl$_2$ for 20 min prior to addition of Chromozym t-PA. The final concentration of the reactants was as follows: 10 nM sTF, 10 nM FVIIa, 0.5 mM Chromozym t-PA. The rates of amidolytic activity were measured at 405 nm on a kinetic microplate reader (Molecular Devices). The background activity was defined as the amidolytic activity of FVIIa in the absence of sTF and was subtracted from the obtained values.

Human Ex-Vivo Thrombosis Model

Tissue factor-expressing human J82 cells (epithelial carcinoma, ATCC HTB1) were grown on Thermanox plastic coverslips as described (Kirchhofer et al., [1995] Arterioscler. Thromb. Vasc. Biol. 15: 1098–1106). The coverslips with the cell monolayer were then positioned in parallel plate perfusion chambers and the entire system including tubings, mixing devices and parallel plate chambers was filled with DMEM-1% (w/v) BSA. The details of the experimental system were described recently (Kirchhofer et al., [1995] supra; Kirchhofer et al., [1994] J. Clin. Invest. 93: 2073–2083). Blood was then drawn from the antecubital vein of a healthy donor at a rate of 1 mL/min. Immediately before entering the mixing chambers the flowing blood was infused with the antibodies at a rate of 50 µL/min by use of an infusion pump (Infu 362, Datex AG, Switzerland). The homogenous blood-antibody mixture then entered three parallel plate perfusion devices containing the J82 cell monolayers. The blood flow of 1 mL/min resulted in a shear rate of 65 s$^{-1}$ on the coverslips which corresponded to venous blood flow conditions. After a 3.5 minute perfusion period the cell layer was washed and coverslips removed for visual inspection of deposited fibrin. Fibrinopeptide A (FPA) levels were measured in the blood leaving the perfusion device as described previously (Kirchhofer et al., [1994] and [1995] supra).

Results

Functionally Different Anti-TF Antibodies

As seen in FIG. 1a, the antibodies 7G11, 6B4 and HTF1 completely inhibited sTF:FVIIa-dependent activity towards Chromozym t-PA, indicating interference with the proper formation of the sTF:FVIIa complex. In contrast, 5G6 antibody did not inhibit at all, whereas D3 reduced activity by about 20%, reaching a plateau at higher concentration. The inhibition by D3 was also seen when the smaller antibody Fab was used (FIG. 1a). The inhibitory effect of D3 was dependent on low sTF concentrations, since no inhibition occurred at high sTF concentrations (120–200 nM) in the presence of molar excess antibody (data not shown). In agreement, D3 did not affect the amidolytic activity when relipidated $TF_{1-243}$ was used, which binds FVIIa with much higher affinity than sTF (data not shown). However, both D3 and 5G6 inhibited TF:FVIIa-mediated activation of macromolecular substrate as well as the other antibodies. This was shown by results obtained from clotting assays in which antibodies were pre-incubated with TF reagent. (FIG. 1b).

Anticoagulant Potencies of Anti-TF Antibodies

The results of the amidolytic assays indicated two fundamentally different types of anti-TF antibodies. Two antibodies of each group (D3 and 5G6 vs 6B4 and HTF1) were selected and their anticoagulant potencies in a human ex-vivo blood flow system determined (Kirchhofer et al., [1994] and [1995] supra). In this system the antibodies were infused to flowing non-anticoagulated human blood, which then entered parallel plate devices containing a monolayer of TF-expressing J82 cells. The shear rate at the cell layer was 65 s$^{-1}$ simulating venous blood flow conditions. In controls this resulted in the generation of fibrinopeptide A (FPA) and the deposition of polymerized fibrin onto the cell monolayer. The average FPA levels of 36 control samples was 1348±46.1 ng/ml plasma (±SEM), which was similar to earlier reported FPA concentrations using the same system (1192±69 ng/ml; (Kirchhofer et al., [1995] supra)). Infusion of D3 and 5G6 potently inhibited FPA generation with $IC_{50}$ values of 16 µg/ml and 50 pg/ml, respectively (FIG. 2). Compared to full length D3, inhibition by the D3 Fab was weaker ($IC_{50}$ 36 µg/ml), most likely due to reduced avidity for surface TF as compared to the bivalent full length D3 antibody. Surprisingly, HTF I antibody did not inhibit at the highest tested concentration of 50 µg/ml, while 6B4 showed rather weak inhibitory activity with about 40% inhibition at 150 µg/ml (FIG. 2). Consistent with the observed reduction of FPA levels by D3, D3 Fab and 5G6, a visual inspection of the cell layers showed that only little if any fibrin was deposited, while HTF1 and 6B4-treated samples were indistinguishable from controls.

Next, the measurement of FX activation in human plasma was used as another way to quantify anticoagulant potencies of the antibodies. Similar to the blood flow system, where antibody is not pre-equilibrated with TF but infused to the flowing blood, the antibodies were added to plasma and coagulation was triggered with relipidated $TF_{1-243}$. We found that the tested antibodies inhibited the initial rates of FX activation in a concentration-dependent manner (FIG. 3). The antibodies D3 and 5G6 were more potent than HTF1, 6B4 and 7G11. The concentrations which inhibited the rates by 50% were as follows: 7.2±1.0 µg/ml (±SD, n=5) for D3, 15.5±1.3 µg/ml (±SD, n=5) for 5G6, 43.4±6.8 µg/ml (±SD, n=4) for 6B4, 147.8±8.6 µg/ml (±SD, n=5) for 7G11 and 150.0±31.1 µg/ml (±SD, n=4) for HTF1.

Furthermore, similar potency differences between the antibodies were found when clotting times were measured in PT assays using the same incubation protocol as for FX activation rate assays (FIG. 4). The antibody concentrations which prolonged the clotting time by 1.5-fold were 10 µg/ml for D3, 27 µg/ml for 5G6, 133 µg/ml for 6B4 and 500 µg/ml for 7G11. The highest tested concentration of HTF1 (40 µg/ml) had no effect (FIG. 4).

Determination of Kinetic Constants of Anti-TF Antibodies

Because the inhibitory potencies of the examined antibodies could merely be a reflection of their binding affinities to sTF, we determined the kinetic constants of each antibody. A comparison of the calculated $K_D$ values (Table 2) and the inhibitory activities of each antibody showed that there is no correlation between affinities and anticoagulant potencies. In fact, D3 was consistently the most potent anticoagulant, yet it displayed the weakest affinity for TF, while HTF1 and 7G11 were the strongest binders, but had the weakest anticoagulant activities. This lack of correlation was also seen when on-rates were compared which, with the exception of HTF1, were in a similar range ($2.3 \times 10^5$–$6.0 \times 10^5 M^{-1} sec^{-1}$).

TABLE 2

| Antibody | $k_{on}$ ($10^5 M^{-1} s^{-1}$) | $k_{off}$ ($10^{-4} s^{-1}$) | $K_D$ (nM) |
|---|---|---|---|
| D3 | 2.43 | 17.3 | 7.00 |
| D3 Fab | 2.40 | 27.5 | 11.50 |
| 5G6 | 3.00 | 5.00 | 1.70 |
| 7G11 | 6.00 | 1.20 | 0.20 |
| 6B4 | 2.26 | 13.4 | 5.90 |
| HTFI | 0.80 | 1.15 | 1.40 |

In addition, competition experiments with FVIIa and sTF showed that in the presence of molar excess of FVIIa (>100x), the antibodies 7G11, 6B4 and HTF1 did not bind to TF, whereas the affinity of D3 and 5G6 was only reduced by 4–5-fold. This was consistent with the results from amidolytic assays (FIG. 1a), indicating that D3 and 5G6 had a fundamentally different inhibitory mechanism than the other antibodies.

Determination of Antibody Epitopes

The results so far indicated that the antibodies' anticoagulant potencies could be related to their specific inhibitory mechanism and, thus, to the precise binding site on TF. To determine the antibody epitopes, a large number of sTF mutants were generated by expression in *E. coli* and subsequent affinity purification on a D3 column (Kelley et al., [1995] supra). The binding of the antibodies to each sTF mutant was measured on a BIAcore instrument. The results, summarized in FIG. 5, show the affinity loss expressed as the ratio of $K_D$ values of sTF mutant and wild-type sTF. Residues that increased the ratio by more than 3-fold were considered important for antibody binding. The two double mutants sTF N199A:R200A and sTF K201A:D204A did not bind to the D3 affinity column and were purified on a 7G11 antibody affinity column. As expected, D3 had the largest loss in affinity to these two mutants ($K_D$ (mut)/$K_D$ (wt) >5000). Since sTF D204A alone had the same affinity to the antibodies as wildtype sTF, we concluded that K201 in the K201A:D204A double mutant was the critical residue for antibody binding. Other residues found to be important for D3 binding were I152, Y156 and K165:K166. With the exception of Y156L, the same sTF mutants also showed decreased binding to the 5G6 antibody.

In contrast to D3 and 5G6 which bound to the C-terminal TF domain, the three antibodies 7G11, 6B4 and HTF1 bound to residues located in the N-terminal TF domain. The TF mutants which had the greatest loss in affinity to 7G11 were K46A (5000×) and Y51A (32×). Additional mutants with significant affinity losses were S47A, K48A, F50A and T52A. The sTF mutants that affected binding of the 6B4 antibody were Y10A, F76A, Y94A, E99A and L104A:E105A. Three of these mutants, F76A, Y94A and E99A, also reduced binding affinity of the HTF1 antibody (FIG. 5).

Location of Antibody Epitopes on the Crystal Structure of the TF:FVIIa Complex

As seen in the crystal structure of the TF:FVIIa complex (Banner et al., [1996] supra), the 7G11 binding site is formed by a clearly defined patch of surface exposed residues with a calculated solvent accessible area of 397 $Å^2$ (FIG. 6). This is relatively small compared to buried surface areas of typical antigens (Huang et al., [1998] supra) and thus, the antibody binding region may not have been identified in its entirety. This region is important for FVIIa binding and the F50 residue makes a critical hydrophobic contact to the second epidermal growth factor domain of FVIIa (Banner et al., [1996] supra).

The TF residues that were important for 6B4 binding defined a large surface area located on the 'back side' of TF as compared to the 7G11 epitope (FIG. 6). With the premise that the epitope is within the perimeter defined by the identified TF residues, the area of the hypothetical epitope was calculated to be 594 $Å^2$. The epitope extended into a TF region which contacts the catalytic domain of FVIIa and included the residues F76 and Y94. For the HTF1 antibody only a relatively small number of TF mutants were examined and the epitope is somewhat less well defined (FIG. 6). Nevertheless, the HTF1 and 6B4 epitopes were largely the same, since three identified binding residues including F76 and Y94 were shared by both antibodies.

The epitopes of the D3 and 5G6 antibodies were very similar, being located outside of the FVIIa-TF contact region. As shown in FIG. 6, the epitope runs from the bottom to the top of the C-terminal TF domain and is approximately opposite to the main TF-FVIIa contact region. Accordingly, antibody binding may not interfere with TF:FVIIa complex formation.

Discussion

By using a large panel of sTF mutants the binding epitopes of 5 anti-TF antibodies was determined and a clear picture of how they exert their anticoagulant effect gained. They bound to three distinct regions of TF and either interfered with FVIIa-TF association (7G11, 6B4, HTF1) or with TF-macromolecular substrate interaction (D3, 5G6). The anticoagulant potencies were determined in whole blood and plasma-based systems in which the antibodies and coagulation factors were allowed to simultaneously interact with TF. First, in the human ex-vivo blood flow system D3 and 5G6 potently inhibited the generation of FPA and the deposition of fibrin onto the J82 cell layer. In contrast, the antibodies 6B4 and HTF1 were at least one order of magnitude less potent and, in the case of HTF1, virtually inactive. Secondly, since coagulation in the blood flow system was shown to proceed via direct TF:FVIIa mediated activation of FX (Kirchhofer et al., [1995] supra), it was reasoned that the differential effects on FPA generation should have a correlate in the inhibition of FX activation rates and prothrombin times in human plasma. Indeed, it was found that D3 and 5G6 were by far the most potent antibodies tested.

The apparent differences in anticoagulant activities could not be explained by differences in the binding affinities of the antibodies. In fact, D3 was the weakest binder ($K_D$ 7 nM) and 7G11 the strongest ($K_D$0.2 nM), yet D3 was about 20-fold more potent in inhibiting FX activation. Because the TF-initiated coagulation is a rapid process it seemed possible that the potency differences reflected differences in on-rates. However, with the exception of HTF1, the experimentally determined on-rates were within a narrow range and showed no correlation with the observed anticoagulant potencies. These findings suggested that the epitope locations rather than on-rate constants or binding affinities were the main determinants of anticoagulant potencies of the anti-TF antibodies.

Inspection of the epitopes on the crystal structure of the TF:FVIIa complex revealed that all antibodies bound to functionally important regions of TF, but impacted different aspects of TF function. The binding epitope of D3 and 5G6 overlapped with a TF region that does not contact FVIIa, but interacts with macromolecular substrate binding. This explained why the antibodies had little or no effect on amidolytic activity towards a small synthetic substrate. The epitope residues K165 and K166 were previously found to be critical for TF:FVIIa mediated activation of FX (Ruf et al., [1992] supra; Roy et al., [1991] supra; Kelley et al., [1995] supra) and FIX (Huang et al., [1996] supra). These two residues and the additional epitope residues Y156 and K201 are all part of a distinct surface-exposed TF region which directly interacts with substrates FX and FIX (Kirchhofer et al., [1999] Thromb. Haemost. Suppl. [abstract], 300; Kirchhofer et al., (2000) Biochemistry 39:7380–7387). This region may extend into the FVIIa Gla domain (Martin et al., [1993] supra; Ruf et al., [1999] supra) and most likely contacts the Gla domains of substrates (Huang et al., [1996] supra; Martin et al., [1993] supra). Thus, D3 and 5G6 by binding to this region will sterically prevent the association of the substrate Gla domains with TF and thus interfere with proper substrate orientation to form a productive ternary TF-FVIIa-substrate complex. This further provided a basis of explaining the excellent anticoagulant potencies of D3 and 5G6. First, since the epitope is not within the TF-FVIIa contact region, these antibodies were able to bind to TF during and after the rapid formation of TF:FVII and TF:FVIIa complexes in plasma. Secondly, they competed with a rather low affinity TF-substrate interaction event. Moreover, the epitope residues K165 and K166 were shown to be important for the FVIIa and FXa-dependent activation of TF:FVII (Dittmar et al., [1997] Biochem. J.

321: 787–793). Therefore, both antibodies could have interfered with the activation of TF-bound zymogen FVII, a reaction which in all likelihood is the first activation step for coagulation in plasma (Rapaport and Rao [1995] Thromb. Haemost. 74: 7–17), as well as in the employed blood flow system with J82 cells (Sakai et al., [1989] J. Biol. Chem. 264: 9980–9988). In fact, D3H44-F(ab')$_2$ was found to strongly inhibit the FXa-mediated activation of zymogen FVII (Kirchhofer et al., (2001) Biochemistry 40:675–682). In agreement, the closely related antibody TF8-5G9 (Morrissey et al., [1988] supra; Ruf and Edgington [1991] supra; Huang et al., [1998] supra; Fiore et al., [1992] supra) which binds to the same TF region (Huang et al., [1998] supra), is a potent anticoagulant in plasma clotting assays (Ruf and Edgington [1991] supra) and inhibits TF-dependent FVII conversion to FVIIa (Fiore et al., [1992] supra). A comparison with TF8-5G9 revealed that all of the identified D3 and 5G6 epitope residues were also found as contact residues in the crystal structure of TF8-5G9 Fab bound to soluble TF (Huang et al., [1998] supra). Yet, despite having an apparently identical epitope the D3 and TF8-5G9 (Fiore et al., [1992] supra) antibodies differed from 5G6 in their ability to weakly inhibit the amidolytic activity (Chromozym t-PA) of the sTF:FVIIa complex at low sTF concentrations. These results indicated that there existed subtle differences in antibody binding to an apparently identical epitope.

The weaker anticoagulant potencies of 7G11, HTF1 and 6B4 were surprising, since they were as potent as D3 and 5G6 when allowed to pre-bind to TF in plasma clotting assays. The identification of the antibody binding sites on TF provided a basis for explaining these results. 7G11 bound to a TF region proximal to the light chain of FVIIa. One of the binding residues, F50, makes an important contact to the second epidermal growth factor domain of FVIIa (Banner et al., [1996] supra; Zhang et al., [1999] J. Mol. Biol. 285: 2089–2104) suggesting that the antibody interfered with the formation of the TF:FVIIa complex. Both 6B4 and HTF1 interfered with a shared FVIIa contact site, which was distinct from the 7G11 epitope. In agreement, 6B4 did not prevent binding of 7G11 to TF in cross-blocking experiments (data not shown). Epitope residues F76 and Y94 make direct contacts to the FVIIa catalytic domain residue Met306. Mutating this Met306 or TF residue Y94 strongly impaired macromolecular substrate activation (Dickinson et al., [1996] supra; Kelley et al., [1995] supra; Ruf et al., [1995] Biochemistry 34: 6310–6315), and binding of 6B4 or HTF1 should consequently have deleterious effects as well. This contact site is also important for the TF-dependent enhancement of FVIIa activity towards small synthetic substrates (Dickinson et al., [1996] supra), thus explaining the observed inhibitory effects of 6B4 and HTF1 in the amidolytic assay. The results are also consistent with a previous report demonstrating that HTF1 interfered with the binding of TF to FVIIa (Carson et al., [1987] supra). There is a possibility that 6B4 had additional effects on the macromolecular substrate-TF interaction. 6B4 did not bind to the main substrate interaction region around K165 and K166 (FIG. 6), but the epitope residues L104:E105 were proximal to residues N 199:R200 which are part of the FX recognition region (Kirchhofer et al., [1999] supra).

Thus, 6B4 binding could have resulted in additional steric effects on substrate-TF interaction.

A distinguishing characteristic of antibodies 7G11, 6B4 and HTF1 is their competition with local FVIIa contact sites within the context of an overall large contact surface (Banner et al., [1996] supra) and high affinity FVII-TF interaction. Whereas this inhibitory mechanism provided potent inhibition in pre-incubation experiments (FIG. 1b), it did not do so under the non-equilibrium conditions of our experimental systems. One likely explanation is that once TF:FVIIa complexes were formed, the antibodies would have little inhibitory effect since inhibition would mainly be determined by the FVIIa/TF off-rate. Similar conclusions were made by Ruf and Edgington (1991, supra) and Fiore et al. (1992, supra) using different in-vitro systems to evaluate two antibodies which interfered with TF-FVIIa association. Nevertheless, at appropriate doses such types of antibodies demonstrated inhibition of the coagulation system in animal experiments (Taylor et al., [1991] Circulatory Shock 33: 127–134; Himber et al., [1997] Thromb. Haemostasis 78: 1142–1149; Pawashe et al., [1994] Circ. Res. 74: 56–63; Ragni et al., [1996] 93: 1913–1918; Thomas et al., [1993] Stroke 24: 847–854; Golino et al., [1996] Nature Med. 2: 35–40). A caveat to this comparison is that the antibodies used for the animal experiments have not been characterized in much detail and no epitope map information is available. Furthermore, the experiments would predict that an antibody like D3 or 5G6 should be efficacious at significantly lower doses. Consistent with this view the closely related TF8-5G9 antibody appeared extremely potent in inhibiting coagulation in a chimpanzee study (Levi et al., [1994] J. Clin. Invest. 93: 114–120) and was also very effective in a tumor metastasis model (Mueller et al., [1992] supra). However, a direct comparison of two well-defined, different type-antibodies has yet to be done.

The findings suggested that the anticoagulant potencies of anti-TF antibodies is not primarily determined by the binding affinity, but rather by the epitope location and consequently by the particular mode of inhibition. Even though the translation of the results obtained from blood/plasma based in-vitro systems into an in-vivo setting has obvious limitations, the findings may nevertheless have some implications in regard to the use of anti-TF antibodies in anticoagulant therapy. As suggested by this study, the choice of an anti-TF antibody may be important in terms of the expected efficacy, since the epitope location will strongly influence the antibody's potency to inhibit thrombosis.

Example 2

Humanization of a Murine Anti-Human Tissue Factor Monoclonal Antibody D3.

Materials and Methods

Cloning of Murine D3

The murine anti-human TF mAb D3 was generated and cloned at Genentech (Paborsky et al., [1990] Prot. Engineering 3: 547–553). Protein sequence analysis of the purified antibody provided an N-terminal sequence for the heavy chain, EVQLQQSGAELVRPGALVKLSCKASGFNIKD (SEQ ID NO: 19), and for the light chain, DIKMTQSPSSM-SASLGESVTITCKASRDIK (SEQ ID NO: 20). Total RNA was purified from D3 hybridoma cell line (1D4(14)_D3) using the standard RNA STAT protocol (Tel-Test-Inc., Friendswood, Tex.). cDNA was made using Oligo dT and Superscript II RNase H-Reverse Transcriptase according to the manufacturers instructions (Gibco BRL, Gaithersburg, Mass.). PCR amplification was performed in a 50 µl reaction using 3 units of UlTma DNA Polymerase (Perkin Elmer, Foster City, Calif.) with 1×buffer, 4 mM MgCl, 40 µM dNTPs, and 0.7–1.0 µM forward and reverse primers. Specific primers used were heavy chain forward, 5'-TACAAACGCGTACGCTGARGTNCARYTNCARCAR WSNGGNGC-3' (SEQ ID NO: 21), heavy chain reverse, 5'-CAGTGGATAGACAGATGGGC CCGTCGTTTTGGC-3' (SEQ ID NO: 22), light chain forward, 5'-GCATACGCTGAYATHAARATGACNCARWSNCC-3' (SEQ ID NO: 23), light chain reverse, 5'-TGGTGCAGCCACGGTCCGTTTKAKYTCCARYTT KGT-3' (SEQ ID NO: 24). Separate reactions were set up for heavy chain and light chain and cycled with the following conditions: 95° for 2 min, 30 cycles of (95° sec, 60° 30 sec, 72° 1 min), 4° hold in a Perkin Elmer 9600. After purification on Qia ¹/₁₀ of the PCR reaction was cloned into pCR-Blunt (Invitrogen). Sequence analysis of the clones revealed that amino acid 7 of both the heavy and light chains were Arg instead of the expected Ser; the codon WSN used in the primers can result in Arg or Ser. The PCR was repeated on individual clones in pCR-Blunt to change the Arg to Ser. The same reverse primers were used and new heavy chain forward primer, 5'-AGGTACAAACGCGTACGCTGAAGT CAACTC-CAGCAAAGTGG-3' (SEQ ID NO: 25) and light chain forward primer, 5'-GCATACGCTGAT ATAAAAATGACG-CAGTCGCCATCC-3' (SEQ ID NO: 26). PCR used UlTma and the same conditions as above. The heavy chain PCR fragment was digested with BsiWI and Apal while the light chain PCR fragment was digested with EcoRV and RsrII. Each resulting digested fragment was cloned into a previously described F(ab) chimeric expression plasmid (Presta et al., Cancer Res. 57: 4593–4599 [1997]).

DNA sequence of heavy chain fragment BsiWI to Apal (SEQ ID NO: 27):

5'-GTACGCTGAAGTGCAACTCCAGCAAAGTGGCGCTGAGCTTGTGAGGC

CAGGGCCTTAGTCAAGTTGTCCTGCAAAGCTTCTGGCTTCAACATTAAAG

ACTACTATATGCACTGGGTGAAGCAGAGGCCTGAACAGGGCCTGGAGTTG

ATTGGATGGATTGATCCTGAGAATGGTAATACTATTTATGACCCGAAGTT

CCAGGACAAGGCCAGTATAACAGCAGACACATCCTCCAACACAGCCTACC

TGCAGCTCAGCAGCCTGACATCTGAGGACACTGCCGTCTATTACTGTGCT

AGAGATACTGCGGCATACTTTGACTACTGGGGCCAAGGCACCACTCTCAC

AGTCTCCTCAGCCAAAACGACGGGCCC-3'

DNA sequence of light chain fragment EcoRV to RsrII (SEQ ID NO: 28):

5'-GATATCAAAATGACGCAGTCGCCATCCTCCATGTCTGCATCGCTGGG

AGAGAGTGTCACTATCACTTGCAAGGCGAGTCGGGACATTAAAAGCTAT

TTAAGCTGGTACCAGCAGAAACCATGGAAATCTCCTAAGACCCTGATCTA

TTATGCCACAAGCTTGGCGGATGGGGTCCCATCAAGATTCAGTGGCAGTG

GATCTGGGCAAGATTATTCTCTAACCATCAGCAGCCTGGAGTCTGACGAT

ACAGCAACTTATTACTGTCTACAGCATGGTGAGAGCCCATTCACGTTCGG

CTCGGGGACAAAGTTGGAACTCAAACGGACCG-3'

Computer Graphics Models of Murine and Humanized F(ab)s

Sequences of the VL and VH domains (SEQ ID NOS: 3 and 1, respectively) were used to construct a computer graphics model of the murine D3 VL-VH domains. This model was used to determine which framework residues should be incorporated into the humanized antibody. A model of the humanized F(ab) was also constructed to verify correct selection of murine framework residues. Construction of models was performed as described previously (Carter et al., Proc. Natl. Acad. Sci. USA 89: 4285–4289 [1992]; Eigenbrot et al., J. Mol. Biol. 229: 969–995 [1993]).

Construction of Humanized F(ab)s

The plasmid pEMXI used for mutagenesis and expression of F(ab)s in *E. coli* has been described previously (Werther et al., J. Immunol. 157: 4986–4995 [1996]). Briefly, the plasmid contains a DNA fragment encoding a consensus human κ subgroup I light chain (VLκI-CL), a consensus human subgroup III heavy chain (VHIII-CH1) and an alkaline phosphatase promoter. The use of the consensus sequences for VL and VH has been described previously (Carter et al., supra).

To construct the first F(ab) variant of humanized D3, F(ab)-1, site-directed mutagenesis (Kunkel, Proc. Natl. Acad. Sci. USA 82: 488–492 [1985]) was performed on a deoxyuridine-containing template of pEMX1. The six CDRs were changed to the murine D3 sequence; the residues included in each CDR were from the sequence-based CDR definitions (Kabat et al., Sequences of proteins of immunological interest, Ed. 5, Public Health Service, National Institutes of Health, Bethesda, Md. [1991] except for CDR-H1 which was defined using a combination of CDR-H1 definitions from Kabat et al. (supra) and Chothia et al., Nature 342:877–833 (1989), i.e., CDR-H1 was defined as extending from residues H26–H35 in the heavy chain). F(ab)-1 therefore consisted of a complete human framework (VL_κ subgroup I and VH subgroup III) with the six complete murine CDR sequences. Plasmids for all other F(ab) variants were constructed from the plasmid template of F(ab)-1. Plasmids were transformed into *E. coli* strain XL-1 Blue (Stratagene, San Diego, Calif.) for preparation of double- and single-stranded DNA. For each variant, DNA coding for light and heavy chains was completely sequenced using the dideoxynucleotide method (Sequenase, U.S. Biochemical Corp., Cleveland, Ohio). Plasmids were transformed into *E. coli* strain 16C9, a derivative of MM294, plated onto Luria broth plates containing 50 µg/ml carbenicillin, and a single colony selected for protein expression. The single colony was grown in 5 ml Luria broth-100 µg/ml carbenicillin for 5–8 h at 37° C. The 5 ml culture was added to 500 ml AP50 µg/ml carbenicillin and allowed to grow for 20 h in a 4 L baffled shake flask at 30° C. AP5 media consists of: 1.5 g glucose, 11.0 g Hycase SF, 0.6 g yeast extract (certified), 0.19 g MgSO4 (anhydrous), 1.07 g NH4Cl, 3.73 g KCl, 1.2 g NaCl, 120 ml 1 M triethanolamine, pH 7.4, to 1 L water and then sterile filtered through 0.1 µm Sealkeen filter. Cells were harvested by centrifugation in a 1 L centrifuge bottle at 3000×g and the supernatant removed. After freezing for 1 h, the pellet was resuspended in 25 ml cold 10 mM Tris-1 mM EDTA-20% sucrose, pH 8.0 250 µl of 0.1 M benzamidine (Sigma, St. Louis, Mo.) was added to inhibit proteolysis. After gentle stirring on ice for 3 h, the sample was centrifuged at 40,000×g for 15 min. The supernatent was then applied to a protein G-Sepharose CL-4B (Pharmacia, Uppsala, Sweden) column (0.5 ml bed volume) equilibrated with 10 mM Tris-1 mM EDTA, pH 7.5. The column was washed with 10 ml of 10 mM Tris-1 mM EDTA, pH 7.5, and eluted with 3 ml 0.3 M glycine, pH 3.0, into 1.25 ml 1 M Tris, pH 8.0. The F(ab) was then buffer exchanged into PBS using a Centricon-30 (Amicon, Beverly, Mass.) and concentrated to a final volume of 0.5 ml. SDS-PAGE gels of all F(ab)s were run to ascertain purity and the concentration of each variant was determined by amino acid analysis. F(ab)s were quantified by measuring $OD_{280}$ and amino acid analysis; concentrations used in assays were from the amino acid analysis.

A chimeric F(ab) was used as the standard in the binding assays. This chimeric F(ab) consisted of the entire murine D3 $V_H$ domain fused to a human CH1 domain at amino acid SerH113 and the entire murine D3 VL domain fused to a human CL domain at amino acid LysL107. Expression and purification of the chimeric F(ab) were identical to that of the humanized F(ab)s.

Construction and Purification of D3H44-F(ab')2

D3H44-F(ab')2 was generated by the addition of the heavy chain hinge (CPPCPAPELLGG) to the C-terminus of the D3H44-F(ab), followed by the GCN4 leucine zipper (51) and a (his)6 tag for purification. D3H44-F(ab')2 was expressed in E. coli and the cell paste was diluted 1:5 (w/v) in 20 mM sodium phosphate pH 7.4, 50 mM NaCl, then lysed using an M110Y microfluidizer (Microfluidics Corp., Newton, Mass.). Polyethylene imine (BASF Corp., Rensselaer, N.Y.) was added to a final concentration of 0.2%, followed by centrifugation (4300×g, 30 min) to remove cellular debris. The supernatant was filtered (0.2 μm) and loaded on to SP Sepharose FF (Amersham Pharmacia Biotech, Uppsala, Sweden) under conditions in which F(ab')2 flowed through. The SP Sepharose FF flow through fraction was applied to Chelating Sepharose FF (Amersham Pharmacia Biotech, Uppsala, Sweden), charged with Cu2+ and equilibrated in 2 mM imidazole, pH 7.0, 250 mM NaCl. D3H44-F(ab')2 was eluted using 200 mM imidazole pH 7.0. The Chelating Sepharose FF elution pool was adjusted to pH 4.0, and the leucine zipper/(his)6 tag was cleaved using pepsin. Following pepsin cleavage, D3H44-F(ab')2 was applied to SP Sepharose High Performance (Amersham Pharmacia Biotech, Uppsala, Sweden) and eluted using a linear gradient from 0 to 0.12 M sodium acetate in 25 mM MES pH 5.6. SP Sepharose High Performance gradient fractions were analyzed by SDS-PAGE and pooled. Finally, D3H44-F(ab')2 was formulated by ultrafiltration using a 10 kDa regenerated cellulose membrane (Millipore Corp., Bedford, Mass.), followed by diafiltration into 20 mM sodium acetate pH 5.5, 0.14 M NaCl. Formulated D3H44-F(ab')2 purity was >99.9% by an E. coli protein impurity assay. The endotoxin level in the formulated D3H44-F(ab')2 was <0.01 EU/mg.

Construction of Chimeric and Humanized IgG

For generation of human IgG2 and IgG4 variants of humanized D3, the humanized VL and VH domains from (F(ab)-D3H44) were subcloned separately into previously described pRK vectors (Eaton et at., Biochemistry 25: 8343–8347) containing the constant domains of human IgG2 or IgG4. The IgG4b variant includes a Ser H241 Pro change that improves formation of the inter-heavy chain disulfides in the hinge, resulting in a more homogeneous production of IgG4 antibody (Augal S. King DJ, Bodmer MW, Turner A, Lawson AD, Roberts G, Pedley b, Adair JR. A single amino acid substitution abolishes the heterogeneity of chimeric mouse/human (IgG4) antibody. Angal et al., Molec. Immunol. 1993;30:105–108; Bloom JW, Madanat Miss., Marriot D, Wong T, Chan S-Y. Iutrachain disultide bond in the core hinge region of human IgG4. Prot. Sci. 1997;6:407–415). The DNA coding for the entire light and the entire heavy chain of each variant was verified by dideoxynuclcotide sequencing. The IgG variants were purified usuig Protein A-Sepharose.

Construction and Purification of IgG1

Tissue Factor Binding Assay.

Maxisorp plates (Nunc, Roskilde, Denmark) were coated overnight at 4° C. with 100 μl/well of 10 μg/ml human soluble tissue factor in coat buffer (50 mM carbonate buffer, pH 9.6). The plates were blocked with 150 μl/well blocking buffer (PBS, 0.5% BSA, pH 7.2) for 1 h at room temperature. The standard and samples were diluted in assay buffer (PBS, 0.5% BSA, 0.05% Tween20, pH 7.2) and incubated on the plates for 2 h at room temperature. 100 μl of 1:10,000 goat anti-human F(ab)-HRP (Cappel, Costa Mesa, Calif.) was added and the plates were incubated for 1 h at room temperature. 100 μl of the substrate 3,3',5,5'-tetramethyl benzidine (TMB) (Kirkegaard & Perry, Gaithersburg, Md.) was added. After 5 min, 100 μl of 1 M $H_3PO_4$ was added to stop the reaction. The plate was washed with wash buffer (PBS, 0.05% Tween 20, pH 7.2) between each step. The absorbance was read at 450 nm on a Titerek stacker reader (ICN, Costa Mesa, Calif.). The standard and samples were fit by Kaleidagraph 3.0.8 (Synergy Software, Reading, Pa.) using a four parameter fit regression. The $OD_{450}$ at the $IC_{50}$ of the standard was determined. The concentration of sample needed to obtain this OD was determined and the ratio of this value versus the $IC_{50}$ of the standard was calculated.

BIAcore™ Biosensor Assays

TF binding of the humanized and chimeric F(ab)s were compared using a BIAcore™ biosensor (Karlsson et al., 1994). Concentrations of F(ab)s were determined by quantitative amino acid analysis. TF was coupled to a CM-5 biosensor chip through primary amine groups according to manufacturer's instructions (Pharmacia). Off-rate kinetics were measured by saturating the chip with F(ab) (35 ml of 2 μM F(ab) at a flow rate of 20 μl/min) and then switching to buffer (PBS-0.05% polysorbate 20). Data points from 0–4500 sec were used for off-rate kinetic analysis. The dissociation rate constant ($k_{off}$) was obtained from the slope of the plot of ln(R0/R) versus time, where R0 is the signal at t=0 and R is the signal at each time point.

On-rate kinetics were measured using two-fold serial dilutions of F(ab) (0.0625-2 μM). The slope, $K_s$, was obtained from the plot of ln(-dR/dt) versus time for each F(ab) concentration using the BIAcore™ kinetics evaluation software as described in the Pharmacia Biosensor manual. R is the signal at time t. Data between 80 and 168, 148, 128, 114, 102, and 92 sec were used for 0.0625, 0.125, 0.25, 0.5, 1, and 2 μM F(ab), respectively. The association rate constant ($k_{on}$) was obtained from the slope of the plot of $K_s$ versus F(ab) concentration. At the end of each cycle, bound F(ab) was removed by injecting 5 μl of 50 mM HCl at a flow rate of 20 μl/min to regenerate the chip.

Bioassays

Reagents

F.IX was from Haematologic Technologies Inc., (Ussex Jct., VT) and F.X was from Enzyme Research Laboratories (South Bend, Ind.). Dioleoyl 1,2-diacyl-sn-glycero-3-(phospho-L-serine) (PS) and oleoyl 1,2-diacyl-sn-glycero-3-phosphocholine (PC) from Avanti Polar Lipids Inc. (Alabaster, Ala.). F.IXa chromogenic substrate #299 was from American Diagnostica (Greenwich, Conn.) and FXa chromogenix substrate S-2765 was from Diapharma Group Inc. (Columbus, Ohio). Innovin was obtained from Dade International Inc. (Miami, Fla.). Ethyleneglycol (analytical grade) was from Mallinckrodt Inc. (Paris, Ky.). Fatty acid-free BSA was from Calbiochem (Calbiochem-Novabiochem Corp. La Jolla, Calif.). TF (1-234) lacking the cytoplasmic domain was produced as described (Paborsky et al., (1989) Biochemistry 28:8072; Paborsky et al., (1991) J. Biol. Chem. 266:21911) and relipidated with PC/PC (7:3 molar ratio) according to Mimms et al., (1981) Biochemistry 20:833–840).

Activation of FIX by Membrane Tissue Factor (mTF): FVIIa Complex

Membrane TF (mTF) was prepared from a human embryonic kidney cell line (293) expressing full length TF (1-263) (Kelley et al., Blood 89: 3219–3227 [1997]). The cells were washed in PBS, detached mM EDTA and centrifuged twice (2500 rpm for 10 min). The cell pellet (4-5×10$^7$ cells/ml) was resuspended in Tris, pH 7.5, and homogenized in PBS using a pestle homogenizer, followed by centrifugation (2500 rpm on a Beckman GSA) for 40 min at 4° C. The protein concentration of the cell membrane fraction was determined and the membranes stored in aliquots at −80° C. until use.

Prior to the addition of F.IX, the antibodies were incubated in microtiter tubes (8.8×45 mm, OPS, Petaluma, Calif.) together with mTF and FVIIa in HBSA buffer (20 mM Hepes, pH 7.5, 150 mM NaCl, 5 mM $CaCl_2$, 0.5 mg/ml BSA) for 20 min at room temperature. The final concentration in the reaction mixture for the reactants were as follows: 150 μg/ml mTF (membrane protein concentration), 2 nM FVIIa and 400 nM F.IX in UBSA. 100 μl aliquots of the reaction mixture were taken at 30 s intervals and quenched in 96-well plates (Costar, Corning Inc., Corning, N.Y.) containing 125 μl of 30 mM EDTA-buffer-60% (v/v) ethyleneglycol. After adding 25 μl of 5 mM F.IX substrate #299, F.IXa amidolytic activity was measured at 405 nm on a kinetic microplate reader (Molecular Devices, Menlo Park, Calif.). Inhibition by the tested antibodies was expressed as fractional rates (vi/vo) of F.IXa generation.

Activation of FX by mTF.FVIIa Complex

The experiments were carried out in a similar fashion as described for F.IX activation. The concentration in the reaction mixture of the reactants were as follows: 200 nM FX, 150 μg/ml mTF, 30 pM FVIIa in HBSA. At 30 s intervals, 50 μl aliquots were quenched in 150 μl 20 mM EDTA and the FXa amidolytic activity measured by adding 50 μl of 1.5 mM S-2765.

Results

Transplanting the murine D3 CDRs onto the human framework (VLκ subgroup I, VH subgroup III) (Carter et al., Proc. Natl. Acad. Sci. USA 89: 4285–4289 [1992]; Presta et al., Cancer Res. 57: 4593–4599 [1997]) resulted in a F(ab) which lacked binding to human TF. Based on the computer graphic model of murine D3 F(ab) (FIG. 7), several amino acid residues in the CDRs as well as framework region of light and heavy chains were altered using site-directed mutagenesis in order to optimize antigen binding. The engineered antibody thus evolved, D3H44 F(ab), exhibited acceptable binding and efficacy in all of the biological assays, including the prothrombin time assays FIGS. 10–12. D3H44 has four human-to-murine changes in its heavy chain framework: Gly H49, Ala H67, Ala H71, and Ala H78 (FIG. 8). D33H44 also has one human-to-murine change in its light chain framework, Tyr L71, as well as one change which is neither human nor murine, Val L46. In the CDRs, D3H44 has seven differences from the murine D3 parent: Glu H31 (CDR-H1), Leu H50 and Gln H54 (CDR-H2), Arg L24 and Asn L34 (CDR-L1), Glu L56 (CDR-L2), and Trp L96 (CDR-L3) (FIGS. 8, 9).

Since a crystal structure of huTF-TF8-5G9 (Huang et al., J. Mol. Biol. 275: 873–894 [1998]) was available in the public Protein Data Bank crystal structure database (coordinates PDB1AHW), the effect of altering some of the sequence of the chimeric D3 F(ab) to that of TF8-5G9 was investigated. First, three residues in CDR-H3 were altered: D3Ch Thr96-Ala97-Ala98 to TF8 Asn96-Ser97-Tyr98. This resulted in a 20-fold reduction in binding (20.3±0.69, n=2). Given that these CDR-H3 residues interact with huTF in the crystal structure, the severe reduction in binding was unexpected. Second, in CDR-H2 D3Ch Asp H65 was changed to TF8 Gly; binding was reduced by 14-fold (14.2±2.7, n=3). Inspection of the huTF-TF8 crystal structure shows that residue H65 is not in contact with huTF and the change to Gly should not have affected binding. Taken together, these data suggest that the D3 antibody does not bind to huTF in the same manner as TF8-5G9.

Binding of anti-tissue factor antibodies (IgG1, IgG2, IgG4 and IgG4b) to tissue factor is shown in FIG. 16. Each of *E. coli* produced IgG1 and CHO produced IgG2, IgG4 and IgG4b bound immobilized TF.

Inhibition of the rates of F.X and F.IX activation by full length versions and a F(ab')2 version of the D3H44 antibody are shown in Table 3.

TABLE 3

| Antibody | F.X activation IC50 (nM) | F.IX activation IC50 (nM) |
|---|---|---|
| D3H44 IgG1 (n = 3) | 0.054 | 0.138 |
| D3H44 LgG2 (n = 3) | 0.073 | 0.160 |
| D3H44 IgG4 (n = 3) | 0.059 | 0.107 |
| D3H44 IgG4 b(n = 3) | 0.048 | 0.127 |
| D3H44 F(ab')2 (n = 3) | 0.047 | N/D |

Antibodies were incubated with relip. TF (1-234) (0.04 nM) and F.VIIa (0.04 nM) for 20 min. and the reaction started by adding F.X (200 nM). Aliquots were taken at different time points and quenched in EDTA. In the second stage of the assay, F.Xa activity was measured by adding chromogenic substrate S2765 and monitoring absorbance at 405 nM on a kinetic microplate reader. IC50 values were calculated by non-linear curve fitting using fractional activities (vi/vo) of initial substrate activation rates vs. antibody concentration. For F.IX assays the concentration of reactants was 1 nM relip.TF(1-234), 1 nM FVIIa, 400 nM F.IX. Reaction aliquots were quenched in EDTA-60% (v/v) ethyleneglycol. In the second stage of the assay, F.IXa activity was measured by adding chromogenic substrate #299 and monitoring absorbance at 405 nM on a kinetic microplate reader. IC50 values were calculated as described above for F.X.

Prolongation of clotting time for the full length versions and Fab and F(ab')2 versions of D3H44 are shown in FIG. 17.

All references cited throughout the specification, including the examples, and all references cited therein are hereby expressly incorporated by reference.

What is claimed is:

1. An isolated nucleic acid molecule comprising a sequence encoding an anti-tissue factor antibody heavy chain variable domain of SEQ ID NO: 2 or 5.

2. An isolated nucleic acid molecule comprising a sequence encoding an anti-tissue factor antibody light chain variable domain of SEQ ID NO: 4 or 6.

3. A nucleic acid molecule comprising a sequence encoding a humanized anti-tissue factor antibody comprising a heavy and a light chain variable domain, wherein said heavy chain variable domain comprises hypervariable regions CDR-H1 having the sequence of GFNIKEYYMH (SEQ ID NO:7), CDR-H2 having the sequence of LIDPEQGNTIYDPKFQD (SEQ ID NO:8) and CDR-H3 having the sequence of DTAAYFDY (SEQ ID NO:9).

4. The nucleic acid molecule according to claim 3, wherein the hypervariable regions are provided in a human framework region.

5. The nucleic acid molecule according to claim 4, wherein the heavy chain variable domain has the sequence of SEQ ID NO: 2.

6. The nucleic acid molecule according to claim 3, wherein the light chain variable domain comprises hypervariable regions CDR-L1 having the sequence of RASRDIKSYLN (SEQ ID NO; 10), CDR-L2 having the sequence of YATSLAE (SEQ ID NO: 11) and CDR-L3 having the sequence of LQHGESPWT (SEQ ID NO: 12).

7. The nucleic acid molecule according to claim 6, wherein the hypervariable regions are provided in a human framework region.

8. The nucleic acid molecule according to claim 7, wherein the light chain variable domain has the sequence of SEQ ID NO: 4.

9. An isolated nucleic acid molecule comprising a sequence encoding a humanized antibody heavy chain variable domain comprising hypervariable regions CDR-H1 having the sequence of GFNIKEYYMH (SEQ ID NO: 7), CDR-H2 having the sequence of LIDPEQGNTIYDPKFQD (SEQ ID NO: 8) and CDR-H3 having the sequence of DTAAYFDY (SEQ ID NO: 9), or humanized antibody light chain variable domain comprising hypervariable regions CDR-L1 having the sequence of RASRDIKSYLN (SEQ ID NO: 10), CDR-L2 having the sequence of YATSLAE (SEQ ID NO: 11) and CDR-L3 having the sequence of LQHGESPWT (SEQ ID NO: 12).

10. A vector comprising and capable of expressing the nucleic acid molecule of any one of claims 1–8 and 9.

11. A host cell transformed with the vector of claim 10.

12. A method of producing an antibody comprising the steps of culturing a host cell comprising the nucleic acid molecule according to any one of claims 1–8 and 9 recovering the antibody.

13. The method of claim 12 wherein the nucleic acid molecule encoding the heavy and light chain variable domains is coexpressed in said recombinant host cell.

14. A nucleic acid molecule comprising a sequence encoding an anti-tissue factor antibody heavy chain variable domain of SEQ ID NO:2 and an anti-tissue factor antibody light chain variable domain of SEQ ID NO:4.

15. A nucleic acid molecule comprising a sequence encoding an anti-tissue factor antibody heavy chain variable domain of SEQ ID NO:5 and an anti-tissue factor antibody light chain variable domain of SEQ ID NO:6.

16. A vector comprising and capable of expressing the nucleic acid molecule of claim 14 or 15.

17. A host cell transformed with the vector of claim 16.

18. A method of producing an antibody comprising the steps of culturing a host cell comprising the nucleic acid molecule according to claim 14 or 15 under conditions suitable for expression of the antibody and recovering the antibody.

19. The method of claim 18 wherein the nucleic acid molecule encoding the antibody heavy and light chain variable domains is coexpressed in said recombinant host cell.

* * * * *

UNITED STATES PATENT AND TRADEMARK OFFICE
CERTIFICATE OF CORRECTION

| | | |
|---|---|---|
| PATENT NO. | : 6,703,494 B2 | Page 1 of 1 |
| APPLICATION NO. | : 09/802083 | |
| DATED | : March 9, 2004 | |
| INVENTOR(S) | : Kirchhofer et al. | |

It is certified that error appears in the above-identified patent and that said Letters Patent is hereby corrected as shown below:

Column 57, lines 50-57, Claim No. 3 should read as follows:

3. A nucleic acid molecule comprising a sequence encoding a humanized anti-tissue factor antibody comprising a heavy and a light chain variable domain, wherein said heavy chain variable domain comprises hypervariable regions CDR-H1 having the sequence of GFNIKEYYMH (SEQ ID NO:7), CDR-H2 having the sequence of LIDPEQGNTIYDPKFQD (SEQ ID NO:8) and CDR-H3 having the sequence of DTAAYFDY (SEQ ID NO:9)

Signed and Sealed this
Eighteenth Day of September, 2012

David J. Kappos
*Director of the United States Patent and Trademark Office*

SEQUENCE LISTING

<160> NUMBER OF SEQ ID NOS: 28

<210> SEQ ID NO 1
<211> LENGTH: 117
<212> TYPE: PRT
<213> ORGANISM: Mus Musculus

<400> SEQUENCE: 1

```
    Glu Val Gln Leu Gln Gln Ser Gly Ala Glu Leu Val Arg Pro Gly
    1               5                   10                  15
    Ala Leu Val Lys Leu Ser Cys Lys Ala Ser Gly Phe Asn Ile Lys
                    20                  25                  30
```

-continued

```
        Asp Tyr Tyr Met His Trp Val Lys Gln Arg Pro Glu Gln Gly Leu
                         35                  40                  45
        Glu Leu Ile Gly Trp Ile Asp Pro Glu Asn Gly Asn Thr Ile Tyr
                     50                  55                  60
        Asp Pro Lys Phe Gln Asp Lys Ala Ser Ile Thr Ala Asp Thr Ser
                 65                  70                  75
        Ser Asn Thr Ala Tyr Leu Gln Leu Ser Ser Leu Thr Ser Glu Asp
                         80                  85                  90
        Thr Ala Val Tyr Tyr Cys Ala Arg Asp Thr Ala Ala Tyr Phe Asp
                         95                 100                 105
        Tyr Trp Gly Gln Gly Thr Thr Leu Thr Val Ser Ser
                        110                 115
```

<210> SEQ ID NO 2
<211> LENGTH: 117
<212> TYPE: PRT
<213> ORGANISM: Artificial sequence
<220> FEATURE:
<223> OTHER INFORMATION: humanized heavy chain variable domain

<400> SEQUENCE: 2

```
        Glu Val Gln Leu Val Glu Ser Gly Gly Gly Leu Val Gln Pro Gly
        1               5                  10                  15
        Gly Ser Leu Arg Leu Ser Cys Ala Ala Ser Gly Phe Asn Ile Lys
                        20                  25                  30
        Glu Tyr Tyr Met His Trp Val Arg Gln Ala Pro Gly Lys Gly Leu
                         35                  40                  45
        Glu Trp Val Gly Leu Ile Asp Pro Glu Gln Gly Asn Thr Ile Tyr
                     50                  55                  60
        Asp Pro Lys Phe Gln Asp Arg Ala Thr Ile Ser Ala Asp Asn Ser
                 65                  70                  75
        Lys Asn Thr Ala Tyr Leu Gln Met Asn Ser Leu Arg Ala Glu Asp
                         80                  85                  90
        Thr Ala Val Tyr Tyr Cys Ala Arg Asp Thr Ala Ala Tyr Phe Asp
                         95                 100                 105
        Tyr Trp Gly Gln Gly Thr Leu Val Thr Val Ser Ser
                        110                 115
```

<210> SEQ ID NO 3
<211> LENGTH: 109
<212> TYPE: PRT
<213> ORGANISM: Mus musculus

<400> SEQUENCE: 3

```
        Asp Ile Lys Met Thr Gln Ser Pro Ser Ser Met Ser Ala Ser Leu
        1               5                  10                  15
        Gly Glu Ser Val Thr Ile Thr Cys Lys Ala Ser Arg Asp Ile Lys
                        20                  25                  30
        Ser Tyr Leu Ser Trp Tyr Gln Gln Lys Pro Trp Lys Ser Pro Lys
                         35                  40                  45
        Thr Leu Ile Tyr Tyr Ala Thr Ser Leu Ala Asp Gly Val Pro Ser
                     50                  55                  60
        Arg Phe Ser Gly Ser Gly Ser Gly Gln Asp Tyr Ser Leu Thr Ile
                 65                  70                  75
        Ser Ser Leu Glu Ser Asp Asp Thr Ala Thr Tyr Tyr Cys Leu Gln
                         80                  85                  90
        His Gly Glu Ser Pro Phe Thr Phe Gly Ser Gly Thr Lys Leu Glu
                         95                 100                 105
        Leu Lys Arg Thr
```

<210> SEQ ID NO 4
<211> LENGTH: 109
<212> TYPE: PRT
<213> ORGANISM: Artificial sequence
<220> FEATURE:
<223> OTHER INFORMATION: humanized light chain variable domain

<400> SEQUENCE: 4

```
        Asp Ile Gln Met Thr Gln Ser Pro Ser Ser Leu Ser Ala Ser Val
        1               5                  10                  15
        Gly Asp Arg Val Thr Ile Thr Cys Arg Ala Ser Arg Asp Ile Lys
                        20                  25                  30
        Ser Tyr Leu Asn Trp Tyr Gln Gln Lys Pro Gly Lys Ala Pro Lys
```

```
                      35                   40                      45
        Val Leu Ile Tyr Tyr Ala Thr Ser Leu Ala Glu Gly Val Pro Ser
                     50                   55                      60
        Arg Phe Ser Gly Ser Gly Ser Gly Thr Asp Tyr Thr Leu Thr Ile
                 65                   70                      75
        Ser Ser Leu Gln Pro Glu Asp Phe Ala Thr Tyr Tyr Cys Leu Gln
                         80                   85                      90
        His Gly Glu Ser Pro Trp Thr Phe Gly Gln Gly Thr Lys Val Glu
                         95                      100                     105
        Ile Lys Arg Thr

<210> SEQ ID NO 5
<211> LENGTH: 118
<212> TYPE: PRT
<213> ORGANISM: Mus Musculus

<400> SEQUENCE: 5

Glu Val Leu Leu Gln Gln Ser Gly Pro Glu Leu Val Lys Pro Gly
        1               5                   10                      15
        Ala Ser Val Lys Ile Pro Cys Lys Ala Ser Gly Tyr Thr Phe Thr
                         20                  25                      30
        Glu Tyr Asn Met Asp Trp Val Lys Gln Ser His Gly Lys Ser Leu
                     35                  40                      45
        Glu Trp Ile Gly Asp Ile Asn Pro Asn Gly Asn Thr Ile Tyr
                     50                  55                      60
        Asn Gln Lys Phe Lys Gly Lys Ala Thr Leu Thr Val Asp Lys Ser
                 65                  70                      75
        Ser Thr Thr Ala Tyr Leu Glu Leu Arg Ser Leu Thr Ser Glu Asp
                         80                  85                      90
        Thr Ala Val Tyr Phe Cys Ala Arg Asp His Asp Tyr Tyr Phe Asp
                         95                      100                     105
        Phe Trp Gly Gln Gly Thr Thr Leu Thr Val Ser Ser Ala
                         110                     115

<210> SEQ ID NO 6
<211> LENGTH: 109
<212> TYPE: PRT
<213> ORGANISM: Mus musculus

<400> SEQUENCE: 6

Asp Ile Gln Met Thr Gln Thr Pro Ala Ser Gln Ser Ala Ser Leu
        1               5                   10                      15
        Gly Glu Ser Val Thr Ile Thr Cys Leu Ala Ser Gln Thr Ile Asp
                         20                  25                      30
        Thr Trp Leu Ala Trp Tyr Gln Gln Lys Pro Gly Lys Ser Pro Gln
                     35                  40                      45
        Leu Leu Ile Tyr Ala Ala Thr Ser Leu Ala Asp Gly Val Pro Ser
                     50                  55                      60
        Arg Phe Ser Gly Ser Gly Ser Gly Thr Lys Phe Ser Phe Lys Ile
                 65                  70                      75
        Ser Ser Leu Gln Ala Glu Asp Phe Val Ser Tyr Tyr Cys Gln Gln
                         80                  85                      90
        Pro Tyr Ser Ser Pro Tyr Thr Phe Gly Gly Gly Thr Lys Leu Glu
                         95                      100                     105
        Leu Lys Arg Thr

<210> SEQ ID NO 7
<211> LENGTH: 10
<212> TYPE: PRT
<213> ORGANISM: Mus musculus

<400> SEQUENCE: 7

Gly Phe Asn Ile Lys Glu Tyr Tyr Met His
        1               5                   10

<210> SEQ ID NO 8
<211> LENGTH: 17
<212> TYPE: PRT
<213> ORGANISM: Mus musculus

<400> SEQUENCE: 8
```

-continued

```
      Leu Ile Asp Pro Glu Gln Gly Asn Thr Ile Tyr Asp Pro Lys Phe
        1               5                  10                  15
      Gln Asp
```

<210> SEQ ID NO 9
<211> LENGTH: 8
<212> TYPE: PRT
<213> ORGANISM: Mus musculus

<400> SEQUENCE: 9

```
      Asp Thr Ala Ala Tyr Phe Asp Tyr
        1               5
```

<210> SEQ ID NO 10
<211> LENGTH: 11
<212> TYPE: PRT
<213> ORGANISM: Mus musculus

<400> SEQUENCE: 10

```
      Arg Ala Ser Arg Asp Ile Lys Ser Tyr Leu Asn
        1               5                  10
```

<210> SEQ ID NO 11
<211> LENGTH: 7
<212> TYPE: PRT
<213> ORGANISM: Mus musculus

<400> SEQUENCE: 11

```
      Tyr Ala Thr Ser Leu Ala Glu
        1               5
```

<210> SEQ ID NO 12
<211> LENGTH: 9
<212> TYPE: PRT
<213> ORGANISM: Mus musculus

<400> SEQUENCE: 12

```
      Leu Gln His Gly Glu Ser Pro Trp Thr
        1               5
```

<210> SEQ ID NO 13
<211> LENGTH: 263
<212> TYPE: PRT
<213> ORGANISM: Homo sapiens

<400> SEQUENCE: 13

```
      Ser Gly Thr Thr Asn Thr Val Ala Ala Tyr Asn Leu Thr Trp Lys
        1               5                  10                  15
      Ser Thr Asn Phe Lys Thr Ile Leu Glu Trp Glu Pro Lys Pro Val
                       20                  25                  30
      Asn Gln Val Tyr Thr Val Gln Ile Ser Thr Lys Ser Gly Asp Trp
                       35                  40                  45
      Lys Ser Lys Cys Phe Tyr Thr Thr Asp Thr Glu Cys Asp Leu Thr
                       50                  55                  60
      Asp Glu Ile Val Lys Asp Val Lys Gln Thr Tyr Leu Ala Arg Val
                       65                  70                  75
      Phe Ser Tyr Pro Ala Gly Asn Val Glu Ser Thr Gly Ser Ala Gly
                       80                  85                  90
      Glu Pro Leu Tyr Glu Asn Ser Pro Glu Phe Thr Pro Tyr Leu Glu
                       95                 100                 105
      Thr Asn Leu Gly Gln Pro Thr Ile Gln Ser Phe Glu Gln Val Gly
                      110                 115                 120
      Thr Lys Val Asn Val Thr Val Glu Asp Glu Arg Thr Leu Val Arg
                      125                 130                 135
      Arg Asn Asn Thr Phe Leu Ser Leu Arg Asp Val Phe Gly Lys Asp
                      140                 145                 150
      Leu Ile Tyr Thr Leu Tyr Tyr Trp Lys Ser Ser Ser Ser Gly Lys
                      155                 160                 165
      Lys Thr Ala Lys Thr Asn Thr Asn Glu Phe Leu Ile Asp Val Asp
```

-continued

```
                                    170                 175                 180
            Lys Gly Glu Asn Tyr Cys Phe Ser Val Gln Ala Val Ile Pro Ser
                                185                 190                 195
            Arg Thr Val Asn Arg Lys Ser Thr Asp Ser Pro Val Glu Cys Met
                            200                 205                 210
            Gly Gln Glu Lys Gly Glu Phe Arg Glu Ile Phe Tyr Ile Ile Gly
                        215                 220                 225
            Ala Val Val Phe Val Val Ile Ile Leu Val Ile Ile Leu Ala Ile
                    230                 235                 240
            Ser Leu His Lys Cys Arg Lys Ala Gly Val Gly Gln Ser Trp Lys
                245                 250                 255
            Glu Asn Ser Pro Leu Asn Val Ser
                260

<210> SEQ ID NO 14
<211> LENGTH: 11
<212> TYPE: PRT
<213> ORGANISM: Homo sapiens

<400> SEQUENCE: 14

Pro Lys Asn Ser Ser Met Ile Ser Asn Thr Pro
        1               5                  10

<210> SEQ ID NO 15
<211> LENGTH: 7
<212> TYPE: PRT
<213> ORGANISM: Homo sapiens

<400> SEQUENCE: 15

His Gln Ser Leu Gly Thr Gln
        1               5

<210> SEQ ID NO 16
<211> LENGTH: 8
<212> TYPE: PRT
<213> ORGANISM: Homo sapiens

<400> SEQUENCE: 16

His Gln Asn Leu Ser Asp Gly Lys
        1               5

<210> SEQ ID NO 17
<211> LENGTH: 8
<212> TYPE: PRT
<213> ORGANISM: Homo sapiens

<400> SEQUENCE: 17

His Gln Asn Ile Ser Asp Gly Lys
        1               5

<210> SEQ ID NO 18
<211> LENGTH: 8
<212> TYPE: PRT
<213> ORGANISM: Homo sapiens

<400> SEQUENCE: 18

Val Ile Ser Ser His Leu Gly Gln
        1               5

<210> SEQ ID NO 19
<211> LENGTH: 31
<212> TYPE: PRT
<213> ORGANISM: Mus musculus

<400> SEQUENCE: 19

Glu Val Gln Leu Gln Gln Ser Gly Ala Glu Leu Val Arg Pro Gly
        1               5                  10                  15
```

```
        Ala Leu Val Lys Leu Ser Cys Lys Ala Ser Gly Phe Asn Ile Lys
                     20                  25                  30
        Asp

<210> SEQ ID NO 20
<211> LENGTH: 30
<212> TYPE: PRT
<213> ORGANISM: Mus musculus

<400> SEQUENCE: 20

Asp Ile Lys Met Thr Gln Ser Pro Ser Ser Met Ser Ala Ser Leu
        1               5                  10                  15
        Gly Glu Ser Val Thr Ile Thr Cys Lys Ala Ser Arg Asp Ile Lys
                     20                  25                  30

<210> SEQ ID NO 21
<211> LENGTH: 42
<212> TYPE: DNA
<213> ORGANISM: Homo sapiens
<220> FEATURE:
<221> NAME/KEY: unsure
<222> LOCATION: 22, 28, 37, 40
<223> OTHER INFORMATION: unknown base

<400> SEQUENCE: 21
tacaaacgcg tacgctgarg tncarytnca rcarwsnggn gc           42

<210> SEQ ID NO 22
<211> LENGTH: 33
<212> TYPE: DNA
<213> ORGANISM: Artificial sequence
<220> FEATURE:
<223> OTHER INFORMATION: synthetic primer

<400> SEQUENCE: 22
cagtggatag acagatgggc ccgtcgtttt ggc                     33

<210> SEQ ID NO 23
<211> LENGTH: 32
<212> TYPE: DNA
<213> ORGANISM: Artificial sequence
<220> FEATURE:
<223> OTHER INFORMATION: synthetic primer
<221> NAME/KEY: unsure
<222> LOCATION: 24, 30
<223> OTHER INFORMATION: unknown base

<400> SEQUENCE: 23
gcatacgctg ayathaarat gacncarwsn cc                      32

<210> SEQ ID NO 24
<211> LENGTH: 36
<212> TYPE: DNA
<213> ORGANISM: Artificial sequence
<220> FEATURE:
<223> OTHER INFORMATION: synthetic primer

<400> SEQUENCE: 24
tggtgcagcc acggtccgtt tkakytccar yttkgt                  36

<210> SEQ ID NO 25
<211> LENGTH: 42
<212> TYPE: DNA
<213> ORGANISM: Artificial sequence
<220> FEATURE:
<223> OTHER INFORMATION: synthetic primer

<400> SEQUENCE: 25
```

-continued

```
        aggtacaaac gcgtacgctg aagtgcaact ccagcaaagt gg        42
```

<210> SEQ ID NO 26
<211> LENGTH: 36
<212> TYPE: DNA
<213> ORGANISM: Artificial sequence
<220> FEATURE:
<223> OTHER INFORMATION: synthetic primer

<400> SEQUENCE: 26

```
        gcatacgctg atataaaaat gacgcagtcg ccatcc        36
```

<210> SEQ ID NO 27
<211> LENGTH: 374
<212> TYPE: DNA
<213> ORGANISM: Mus musculus

<400> SEQUENCE: 27

```
        gtacgctgaa gtgcaactcc agcaaagtgg cgctgagctt gtgaggccag  50
        ggccttagtc aagttgtcct gcaaagcttc tggcttcaac attaaagact 100
        actatatgca ctgggtgaag cagaggcctg aacagggcct ggagttgatt 150
        ggatggattg atcctgagaa tggtaatact atttatgacc cgaagttcca 200
        ggacaaggcc agtataacag cagacacatc ctccaacaca gcctacctgc 250
        agctcagcag cctgacatct gaggacactg ccgtctatta ctgtgctaga 300
        gatactgcgg catactttga ctactggggc caaggcacca ctctcacagt 350
        ctcctcagcc aaaacgacgg gccc 374
```

<210> SEQ ID NO 28
<211> LENGTH: 328
<212> TYPE: DNA
<213> ORGANISM: Mus musculus

<400> SEQUENCE: 28

```
        gatatcaaaa tgacgcagtc gccatcctcc atgtctgcat cgctgggaga  50
        gagtgtcact atcacttgca aggcgagtcg ggacattaaa agctatttaa 100
        gctggtacca gcagaaacca tggaaatctc ctaagaccct gatctattat 150
        gccacaagct tggcggatgg ggtccatca agattcagtg cagtggatc 200
        tgggcaagat tattctctaa ccatcagcag cctggagtct gacgatacag 250
        caacttatta ctgtctacag catggtgaga gcccattcac gttcggctcg 300
        gggacaaagt tggaactcaa acggaccg 328
```